(12) United States Patent
Hayes et al.

(10) Patent No.: US 11,629,377 B2
(45) Date of Patent: Apr. 18, 2023

(54) ERROR DETECTION DURING HYBRIDISATION OF TARGET DOUBLE-STRANDED NUCLEIC ACID

(71) Applicant: EVONETIX LTD, Cambridge (GB)

(72) Inventors: Matthew James Hayes, Cambridge (GB); Raquel Maria Sanches-Kuiper, Cambridge (GB); Daniel Adrian Bygrave, Cambridge (GB)

(73) Assignee: EVONETIX LTD, Cambridge (GB)

( * ) Notice: Subject to any disclaimer, the term of this patent is extended or adjusted under 35 U.S.C. 154(b) by 338 days.

(21) Appl. No.: 16/647,939

(22) PCT Filed: Sep. 27, 2018

(86) PCT No.: PCT/GB2018/052753
§ 371 (c)(1),
(2) Date: Mar. 17, 2020

(87) PCT Pub. No.: WO2019/064006
PCT Pub. Date: Apr. 4, 2019

(65) Prior Publication Data
US 2020/0248254 A1    Aug. 6, 2020

(30) Foreign Application Priority Data

Sep. 29, 2017 (GB) .................................... 1715852
Dec. 20, 2017 (GB) .................................... 1721441

(51) Int. Cl.
*C12Q 1/6874* (2018.01)
*B01J 19/00* (2006.01)
(Continued)

(52) U.S. Cl.
CPC ........ *C12Q 1/6874* (2013.01); *B01J 19/0046* (2013.01); *C12N 15/1031* (2013.01);
(Continued)

(58) Field of Classification Search
None
See application file for complete search history.

(56) References Cited

U.S. PATENT DOCUMENTS 6,099,803 A    8/2000  Ackley et al.
6,586,211 B1   7/2003  Stähler et al.
(Continued)

FOREIGN PATENT DOCUMENTS

EP    0 385 410    9/1990
EP    1411 122     7/2008
(Continued)

OTHER PUBLICATIONS

Charles L. Asbury, et al., "Trapping of DNA by dielectrophoresis", Electrophoresis, 2002, vol. 23, pp. 2658-2666.
(Continued)

*Primary Examiner* — Kaijiang Zhang
(74) *Attorney, Agent, or Firm* — Nixon & Vanderhye P.C.

(57) ABSTRACT

A series of hybridisations is performed for forming a target double-stranded nucleic acid from initial fragments, where each further hybridisation step hybridises the direct products of a pair of earlier hybridisation steps. For at least one further hybridisation step $H_F$, both of the corresponding pair of earlier hybridisation steps $H_E$ comprise an error-detecting type of hybridisation step, which includes an error detecting operation to detect whether the hybridised fragments formed in the error-detecting type of hybridisation step $H_E$ comprise at least one erroneous hybridised fragment, and discarding at least part of the erroneous fragment to exclude it from a subsequent further hybridisation step. By detecting and removing erroneous fragments throughout a staged and controlled hybridisation process, erroneous fragments are (Continued)

prevented from diluting the pool of error-free fragments at each hybridisation step, to improve yield.

23 Claims, 19 Drawing Sheets

Specification includes a Sequence Listing.

(51) Int. Cl.
  *C12N 15/10* (2006.01)
  *C12Q 1/6834* (2018.01)
(52) U.S. Cl.
  CPC ... *C12Q 1/6834* (2013.01); *B01J 2219/00274* (2013.01); *C12Q 2527/107* (2013.01); *C12Q 2545/107* (2013.01)

(56) References Cited

U.S. PATENT DOCUMENTS

| | | | |
|---|---|---|---|
| 6,685,812 | B2 | 2/2004 | Miles |
| 7,323,320 | B2 | 1/2008 | Oleinikov |
| 7,790,369 | B2 | 9/2010 | Stähler et al. |
| 7,879,580 | B2 | 2/2011 | Carr et al. |
| 9,568,839 | B2 | 2/2017 | Stähler et al. |
| 2002/0028444 | A1 | 3/2002 | Harney et al. |
| 2004/0235035 | A1 | 11/2004 | Lathrop et al. |
| 2005/0059029 | A1 | 3/2005 | Mariella, Jr. et al. |
| 2005/0191623 | A1 | 9/2005 | Jarrell et al. |
| 2007/0004041 | A1 | 1/2007 | Church et al. |
| 2007/0031857 | A1 | 2/2007 | Makarov et al. |
| 2007/0087417 | A1 | 4/2007 | Namsaraev |
| 2007/0172839 | A1 | 7/2007 | Smith et al. |
| 2009/0036325 | A1 | 2/2009 | McKernan et al. |
| 2009/0305233 | A1 | 12/2009 | Borovkov et al. |
| 2011/0082055 | A1 | 4/2011 | Fox et al. |
| 2011/0124049 | A1 | 5/2011 | Li et al. |
| 2012/0156731 | A1 | 6/2012 | Huang et al. |
| 2014/0248703 | A1 | 9/2014 | Chang et al. |
| 2015/0203839 | A1 | 7/2015 | Jacobson et al. |
| 2015/0376602 | A1 | 12/2015 | Jacobson et al. |
| 2016/0251663 | A1 | 9/2016 | Chang et al. |

FOREIGN PATENT DOCUMENTS

| | | | |
|---|---|---|---|
| EP | 1 314 783 | | 11/2008 |
| EP | 2 110 435 | | 10/2009 |
| EP | 1 557 464 | | 9/2010 |
| EP | 3 375 876 | | 9/2018 |
| JP | 2008-523786 | | 7/2008 |
| JP | 2008-526259 | | 7/2008 |
| WO | 98/38296 | | 9/1998 |
| WO | 98/38298 | | 9/1998 |
| WO | 98/38326 | | 9/1998 |
| WO | 99/02725 | | 1/1999 |
| WO | 99/14318 | | 3/1999 |
| WO | 00/63360 | | 10/2000 |
| WO | 00/75368 | | 12/2000 |
| WO | 01/07633 | | 2/2001 |
| WO | 01/81568 | | 11/2001 |
| WO | 01/83826 | | 11/2001 |
| WO | 02/081490 | | 10/2002 |
| WO | 02/099080 | | 12/2002 |
| WO | 03/038404 | | 5/2003 |
| WO | 2004/024886 | | 3/2004 |
| WO | 2004/027082 | | 4/2004 |
| WO | 2005/059096 | | 6/2005 |
| WO | 2005/059097 | | 6/2005 |
| WO | 2005/089110 | | 9/2005 |
| WO | 2006/026614 | | 3/2006 |
| WO | 2006/044956 | | 4/2006 |
| WO | WO-2006044956 A1 * | 4/2006 | ............ C12N 15/10 |
| WO | 2006/049843 | | 5/2006 |
| WO | 2006/053131 | | 5/2006 |
| WO | 2006/127423 | | 11/2006 |
| WO | 2006/138284 | | 12/2006 |
| WO | 2007/065035 | | 6/2007 |
| WO | 2007/120624 | | 10/2007 |
| WO | 2007/123742 | | 11/2007 |
| WO | 2007/136834 | | 11/2007 |
| WO | 2007/137242 | | 11/2007 |
| WO | 2007/142608 | | 12/2007 |
| WO | 2008/027452 | | 3/2008 |
| WO | 2008/054543 | | 5/2008 |
| WO | 2008/058282 | | 5/2008 |
| WO | 2009/103027 | | 8/2009 |
| WO | 2009/138954 | | 11/2009 |
| WO | 2010/070295 | | 6/2010 |
| WO | 2011/053987 | | 5/2011 |
| WO | 2011/150168 | | 12/2011 |
| WO | 2012/044847 | | 4/2012 |
| WO | 2012/078312 | | 6/2012 |
| WO | 2014/004393 | | 1/2014 |

OTHER PUBLICATIONS

Peter A. Carr, et al., "Genome engineering", Nature Biotechnology, Review, vol. 27, No. 12, Dec. 2009, pp. 1151-1162.
Sriram Kosuri, et al., "Scalable gene synthesis by selective amplification of DNA pools from high-fidelity microchips", Nature Biotechnology, Letters, vol. 28, No. 12, Dec. 2010, pp. 1295-1299.
Jingdong Tian, et al., "Accurate multiplex gene synthesis from programmable DNA microchips", Nature, vol. 432, No. 7020, Dec. 23, 2004, pp. 1050-1054.
Ai-Sheng Xiong, et al., "Non-polymerase-cycling-assembly-based chemical gene synthesis: Strategies, methods and progress", Biotechnology Advances, ElSevier, vol. 26, No. 2, Nov. 7, 2007, pp. 121-134.
Tuval Ben Yehezkel, et al., "Recursive Construction and Error Correction of DNA Molecules and Libraries From Synthetic and Natural DNA", Methods in Enzymology, Academic Press Inc., Ltd., vol. 498, 2011, 40 pages.
Combined Search and Examination Report for GB Application No. 1721441.2 dated Apr. 1, 2019, 6 pages.
Combined Search and Examination Report for GB Application No. 1715852.8 dated Jul. 13, 2018, 6 pages.
International Search Report and Written Opinion of the ISA for PCT/GB2018/052753 dated Nov. 28, 2018, 16 pages.
Office Action for JP Application No. 2020-517439 dated Apr. 26, 2022, 3 pages.
Office Action for EP Application No. 18782786.0 dated Jul. 28, 2021, 6 pages.
J-M Zhang et al, "One step to construct homologous arm vector containing multi-DNA fragments" Shengwu Jishu Tongxun, vol. 24, 2013, English abstract, 1 page.
R-Y Wang et al, "Cloning Large Gene Clusters from *E. coli* Using in Vitro Single-Strand Overlapping Annealing" ACS Synthetic Biology, Jun. 11, 2012, pp. 291-295.
D.G. Gibson, "Enzymatic Assembly of Overlapping DNA Fragments" Methods in Enzymology, 2011, vol. 498, (Synthetic Biology, Part B) pp. 349-361.
D.R. Horspool et al, "Efficient assembly of very short oligonucleotides using T4 DNA Ligase" BMC Research Notes, 3:291, Nov. 9, 2010, 9 pages.
D.G. Gibson et al, "Chemical synthesis of the mouse mitochondrial genome" Nature Methods, vol. 7, No. 11, Nov. 2010, 6 pages.
S.M. Lippow et al, "Creation of a type IIS restriction endonuclease with a long recognition sequence" Nucleic Acids Research, vol. 37, No. 9, Mar. 20, 2009, pp. 3061-3073.
K. Cai et al, "Pre-merged Repeats Masking-off Method in DNA Fragment Assembly" Computer Engineering, vol. 35, No. 4, Feb. 2009, pp. 88-90.
D.G. Gibson et al, "Enzymatic assembly of DNA molecules up to several hundred kilobases" Nature Methods, vol. 6, No. 5, May 2009, 5 pages.
L.S.Z. Larsen et al, "Computationally Optimised DNA Assembly of synethetic genes" International Journal of Bioinformatics Research and Applications, 2008, 4(3), Apr. 13, 2009, 15 pages.

(56) References Cited

OTHER PUBLICATIONS

J. Van den Brulle et al, "A novel solid phase technology for high-throughput gene synthesis" BioTechniques, vol. 45, No. 3, Sep. 2008, pp. 340-343.

M. van den Hout et al, "End-joining long nucleic acid polymers" Nucleic Acids Research, 2008, vol. 36, No. 16, Jul. 25, 2008, pp. 1-8.

X-X. Li et al, "An Alternative Approach to Synthesize cDNA Bypassing Traditional Reverse Transcription" Molecular Biotechnology, 2008, vol. 39, Jan. 29, 2008, pp. 201-206.

C. Pistol et al, "Scalable, low-cost, hierarchical assembly of programmable DNA nanostructures" Nanotechnology, vol. 18, Feb. 23, 2007, 5 pages.

H. Sanchez et al, "Dynamic structures of *Bacillus subtilis* RecN-DNA complexes" Nucleic Acids Research, vol. 36, No. 1, Nov. 13, 2007, pp. 110-120.

N. Ramalanjaona et al, "Investigating the Mechanism of the Nucleocapsid Protein Chaperoning of the Second Strand Transfer during HIV-1 DNA Synthesis" Journal of Molecular Biology (2007), vol. 374, Oct. 5, 2007, pp. 1041-1053.

B. Dong et al, "An Improved Method of Gene Synthesis Based on DNA Works Software and Overlap Extension PCR" Molecular Biotechnology, Dec. 2007, 7 pages.

D.S. Kong et al, "Parallel gene synthesis in a microfluidic device" Nucleic Acids Research, 2007, vol. 35, No. 8, Apr. 2, 2007, pp. 1-9.

A-S. Xiong et al, "PCR-based accurate synthesis of long DNA sequences" Nature Protocols, vol. 1, No. 2, Feb. 2006, 8 pages.

K. Zahradka et al, "Reassembly of shattered chromosomes in *Deinococcus radiodurans*" Nature, vol. 443, Oct. 2006, 6 pages.

R. Peytavi et al, "Correlation between microarray DNA hybridization efficiency and the position of short capture probe on the target nucleic acid" BioTechniques, vol. 39, No. 1, Jul. 2005, pp. 89-96.

F. Dahl et al, "Multiplex amplification enabled by selective circularization of large sets of genomic DNA fragments" Nucleic Acids Research, 2005, vol. 33, No. 8, Apr. 28, 2005, pp. 1-7.

J.M. Daley et al, "Rejoining of DNA Double-Strand Breaks as a Function of Overhang Length" Molecular and Cellular Biology, Feb. 2005, vol. 25, No. 3, pp. 896-906.

J-M. Rouillard et al, "Gene2Oligo: oligonucleotide design for in vitro gene synthesis" Nucleic Acids Research, 2004, vol. 32, Web Server issue, Jul. 2004, 5 pages.

O. Ericsson et al, "Microarray-based resequencing by apyrase-mediated allele-specific extension" Electrophoresis 2003, vol. 24, Oct. 27, 2003, pp. 3330-3338.

R.M. Horton et al, "A T-Linker Strategy for Modification and Directional Cloning of PCR Products" Methods in Molecular Biology, vol. 226, PCR Protocols, Second Edition, 2003, pp. 475-483.

D. Yu et al, "Recombineering with overlapping single-stranded DNA oligonucleotides: Testing a recombination intermediate" Proceedings of the National Academy of Sciences USA, vol. 100, No. 12, Jun. 10, 2003, pp. 7207-7212.

C.J. Nulf et al, DNA assembly using bis-peptide nucleic acids (bisPNAs), Nucleic Acids Research, vol. 30, No. 13, Aug. 2002, 9 pages.

N.E. Broude et al, "DNA microarrays with stem-loop DNA probes: preparation and applications" Nucleic Acids Research, 2001, vol. 29, No. 19, Oct. 2001, pp. 1-11.

V.R. Chechetkin et al, "Sequencing by Hybridization with the Generic 6-mer Oligonucleotide Microarray: An Advanced Scheme for Data Processing" Journal of Biomolecular Structure and Dynamics, vol. 18, No. 1, Aug. 2000, 20 pages.

Y.P. Lysov et al, "Efficiency of sequencing by hybridization on oligonucleotide matrix supplemented by measurement of the distance between DNA segments" DNA Sequence, vol. 6, 1996, Issue 2, Jul. 11, 2009, Abstract, 3 pages.

P.K. Singh et al, "A facile method for the construction of synthetic genes" Journal of Biosciences, vol. 21, No. 6, Dec. 1996, pp. 735-741.

R.A.O. Bennett et al, "Construction of a vector containing a site-specific DNA double-strand break with 3-phosphoglycolate termini and analysis of the products of end-joining in CV-1 cells" International Journal of Radiation Biology, vol. 70, Issue 6, Abstract, 1996, 4 pages.

N.E. Broude et al, "Enhanced DNA sequencing by hybridization" Proceedings of the National Academy of Sciences USA, vol. 91, Apr. 1994, pp. 3072-3076.

A.B. Chetverin et al, "Sequencing of pools of nucleic acids on oligonucleotide arrays" Biosystems, vol. 30, Issues 1-3, 1993, Abstract, 2 pages.

K.R. Khrapko et al, "An oligonucleotide hybridization approach to DNA sequencing" FEBS Letters, vol. 256, No. 1, 2, Oct. 1989, pp. 118-122.

J.C.S. Clegg, "Assembly of Genes from Partially Overlapping Fragments Using Single-Stranded DNA and Sequence-Specific Synthetic Oligodeoxynucleotides" Analytical Biochemistry, vol. 181, Feb. 21, 1989, pp. 106-108.

S. Kosuri et al, "Scalable gene synthesis by selective amplification of DNA pools from high-fidelity microchips" Nature Biotechnology, vol. 28, No. 12, Nov. 28, 2010, 7 pages.

W.P.C. Stemmer, "DNA shuffling by random fragmentation and reassembly: In vitro recombination for molecular evolution" Proceedings of the National Academy of Sciences, vol. 91, Oct. 1994, pp. 10747-10751.

A.Y. Borovkov et al, "High-quality gene assembly directly from unpurified mixtures of microarray-synthesized oligonucleotides" Nucleic Acids Research, vol. 38, No. 19, Aug. 6, 2010, pp. 1-10.

J.J. Schwartz et al., "Accurate gene synthesis with tag-directed retrieval of sequence-verified DNA molecules" Nature Methods, vol. 9, No. 9, Aug. 12, 2012, pp. 913-917.

\* cited by examiner

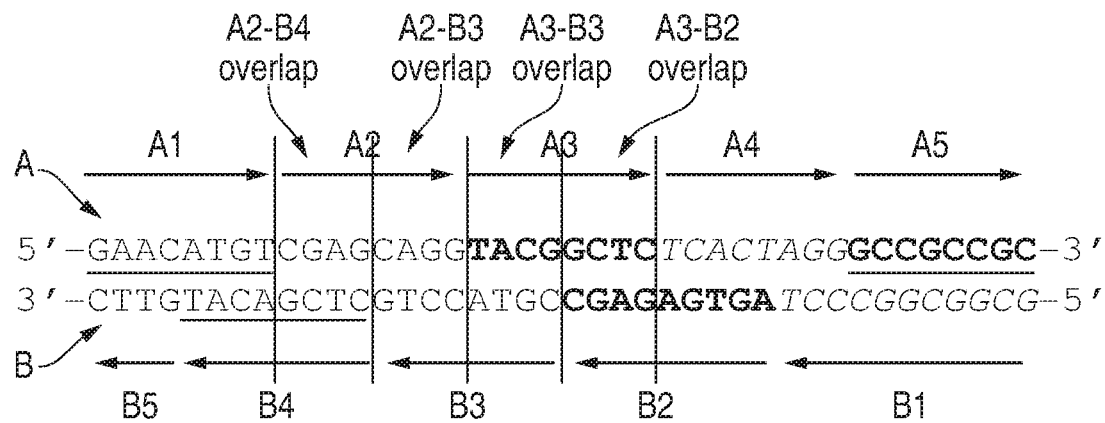
FIG. 1
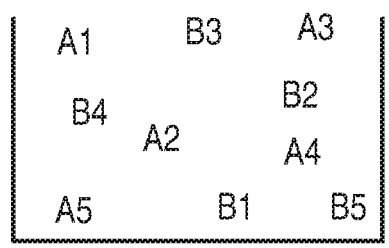
FIG. 2

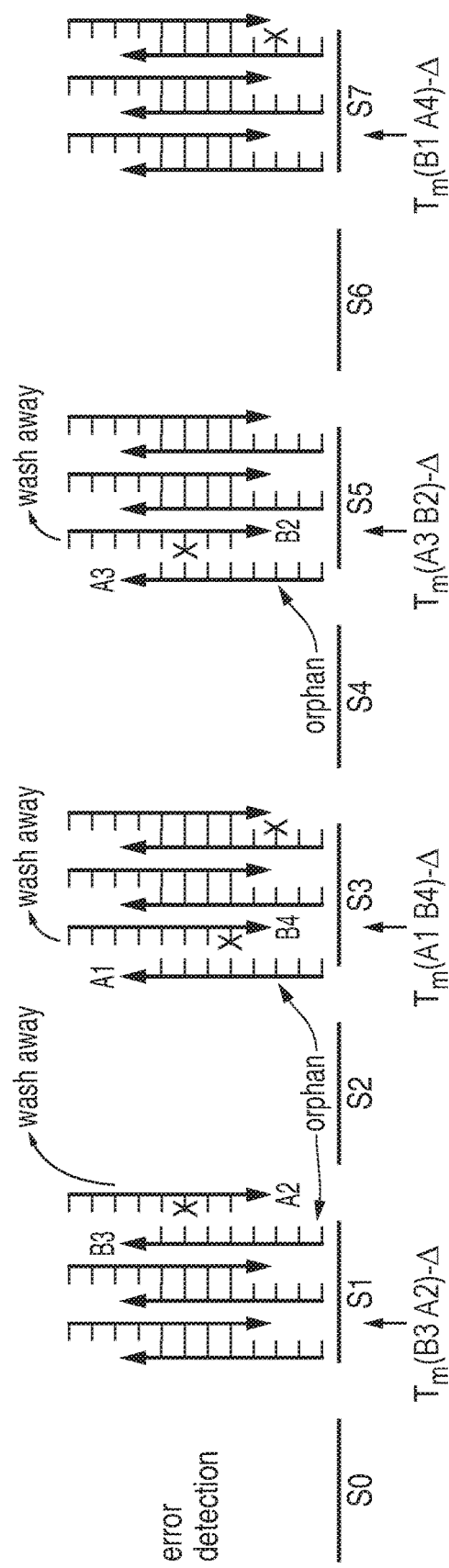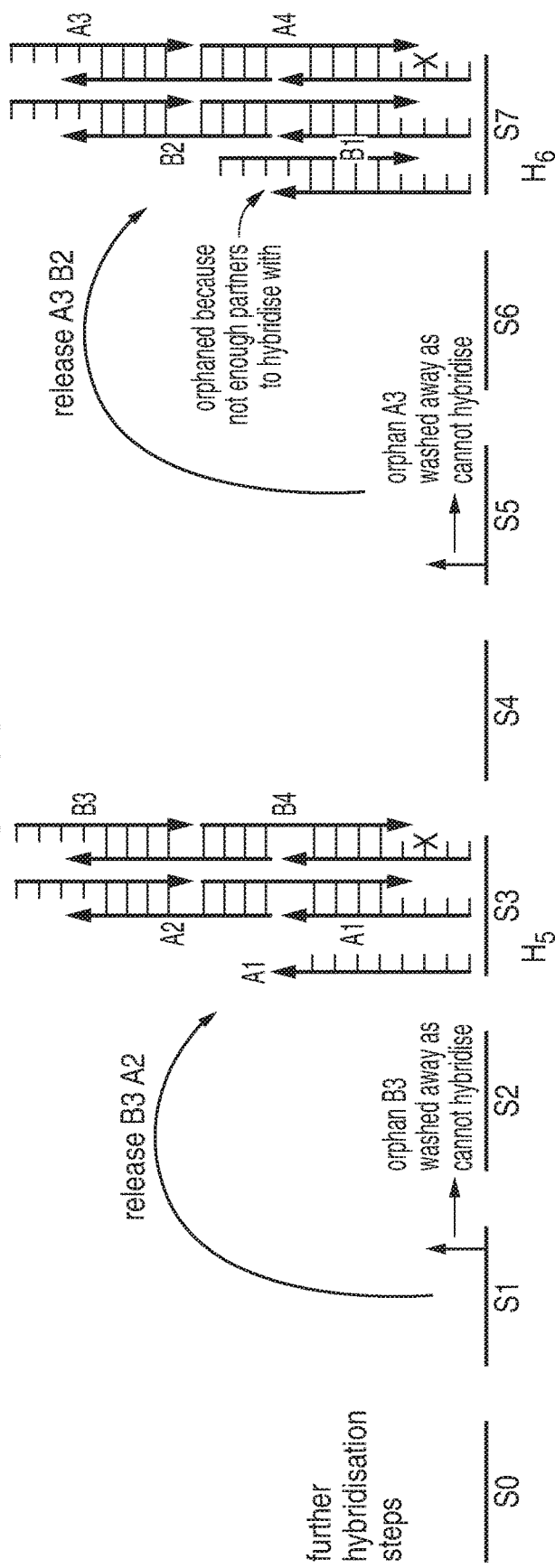
FIG. 13C
FIG. 13D

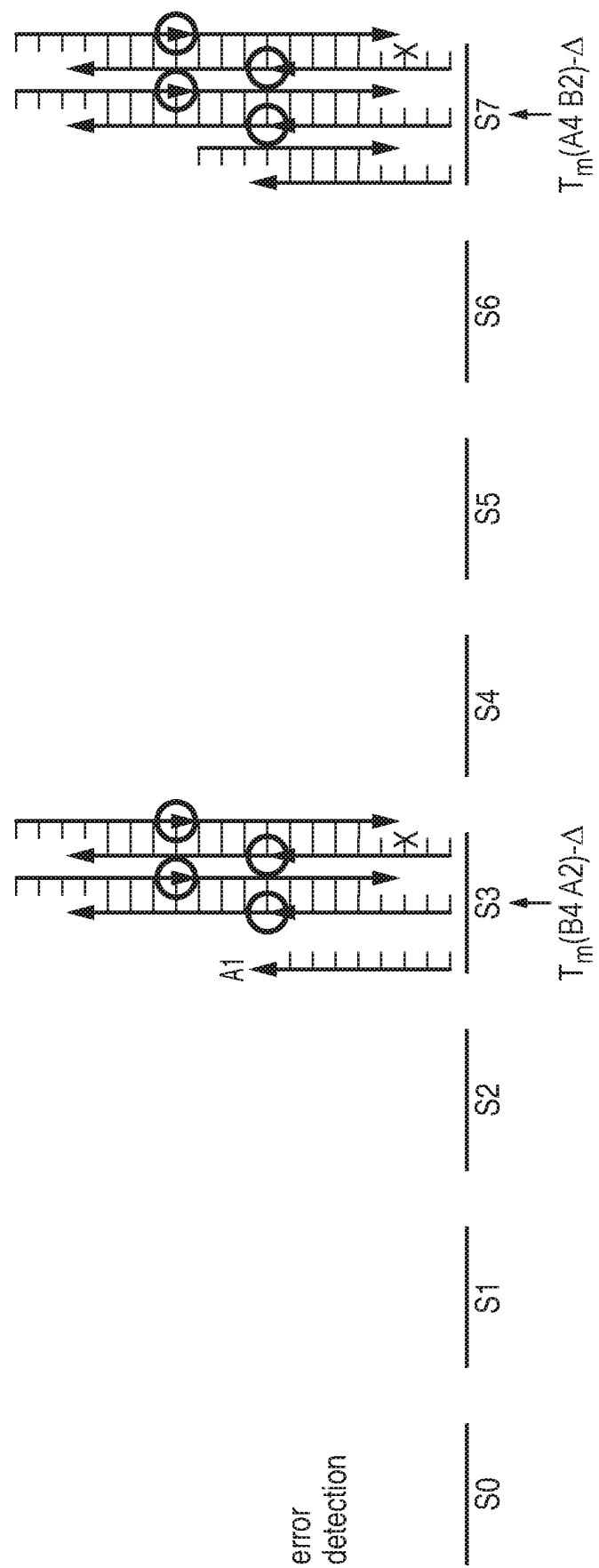

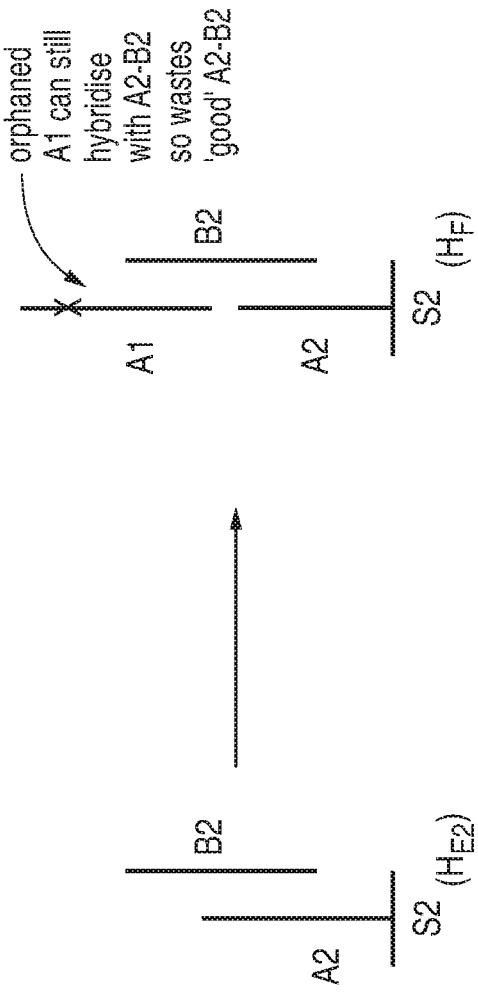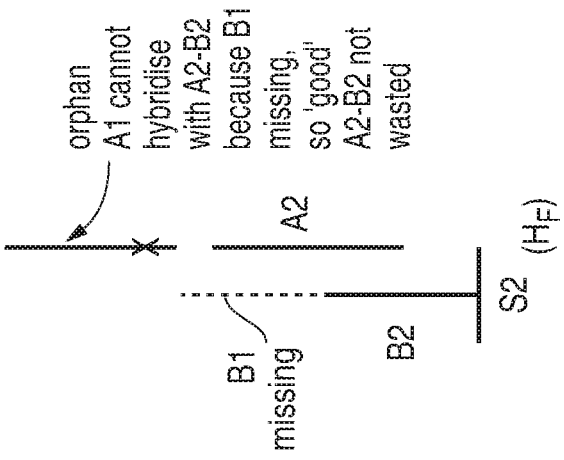
FIG. 14A
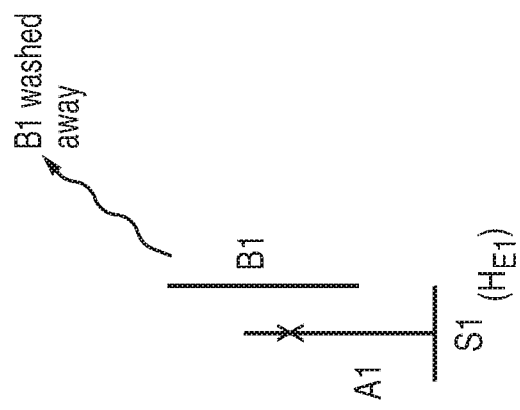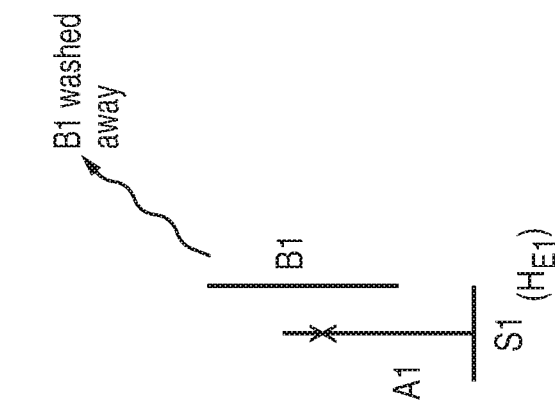
FIG. 14B

5'-ATGGTGAGCAAGGGCGAGGAGCTGTTCACCGGGGTGGTGCCCATCCTGGTCGAGCTGGACGGCGACGTAAAGGAGCTGTGTTCACCGGGGTGGTGAGGAGCTG-3'

(s1) 5'-ATGGTGAGCAAGGGCGAGGAGCTGTTCACCGGGG-3'
(a1) 3'-TACCACTCGTTCCCGCTCCTCGACAAGTGGCCCCACCAGGGTAGGACCAGCTCGACCTGCCGCTGC-5'

(s2)                                    5'-TGGTGCCCATCCTGGTCGAGCTGGACGGCGACGTAAGGAGCTGTTCACCGGGTGGTGAGGAGCTG-3'
(a2)                                                                                        3'-ATTCCTCGACAAGTGGCCCCACCACTCCTCGAC-5'

Hybridisation 1: melt temperature of overlap 0 (between s1 and a1) = 76.9 degC
5'-ATGGTGAGCAAGGGCGAGGAGCTGTTCACCGGGG
3'-TACCACTCGTTCCCGCTCCTCGACAAGTGGCCCCACCAGGGTAGGACCAGCTCGACCTGCCGCTGC-5'

Hybridisation 2: melt temperature of overlap 1 (between a1 and s2) = 78.3 degC
5'-ATGGTGAGCAAGGGCGAGGAGCTGTTCACCGGGG<u>TGGTGCCCATCCTGGTCGAGCTGGACGGCGACGTAAGGAGCTGTTCACCGGGGTGGTGAGGAGCTG</u>-3'
3'-TACCACTCGTTCCCGCTCCTCGACAAGTGGCCCCACCAGGGTAGGACCAGCTCGACCTGCCGCTGC-5'

Hybridisation 3: melt temperature of overlap 2 (between s2 and a2) = 73.7 degC
5'-ATGGTGAGCAAGGGCGAGGAGCTGTTCACCGGGGTGGTGCCCATCCTGGTCGAGCTGGACGGCGACGTAAGGAGCTGTTCACCGGGGTGGTGAGGAGCTG-3'
3'-TACCACTCGTTCCCGCTCCTCGACAAGTGGCCCCACCAGGGTAGGACCAGCTCGACCTGCCGCTGACC<u>ATTCCTCGACAAGTGGCCCCACCACTCCTCGAC</u>

FIG. 18

ERROR DETECTION DURING HYBRIDISATION OF TARGET DOUBLE-STRANDED NUCLEIC ACID

This application is the U.S. national phase of International Application No. PCT/GB2018/052753 filed Sep. 27, 2018 which designated the U.S. and claims priority to GB Application No. 1715852.8 filed Sep. 29, 2017, and GB Application No. 1721441.2 filed Dec. 20, 2017, the entire contents of each of which are hereby incorporated by reference.

The present technique relates to the hybridisation of nucleic acid fragments to form a target double-stranded nucleic acid, for example in the field of artificial synthesis of DNA or other double-stranded nucleic acids.

There is an increasing demand for artificial or synthetic synthesis of double-stranded nucleic acids such as DNA, RNA or XNA. By enabling target sequences of double-stranded nucleic acids to be synthesised de novo in a factory or lab, rather than, for example, relying on cloning-based techniques to replicate portions of existing double-stranded nucleic acids, the cost of producing target sequences of double-stranded nucleic acid can be greatly reduced and the speed with which sequences can be generated can be improved. Typically, single-stranded nucleic acid fragments, such as oligonucleotides, can be manufactured by incorporating the desired nucleotides into sequences, for example using chemical (e.g. phosphoramidite coupling chemistry) and/or enzymatic means (e.g. modified terminal deoxynucleotidyl transferases). The initial batch of single-stranded nucleic acid fragments can be selected so that they have overlap regions comprising complementary sequences of nucleotides (bases) so are likely to hybridise in the correct order when the respective fragments are brought together.

However, incorporation of nucleotides into oligonucleotides inherently includes errors which occur with a random distribution throughout the single-stranded nucleic acid fragments. For example, errors may occur due to the incorporation of a wrong base into the oligonucleotides, due to insertion of an additional base into the oligonucleotides, due to a truncation where a certain oligonucleotide stops growing beyond a certain point when at least one further base should have been added, or due to deletions where a certain base of the fragment is omitted and then the fragment continues to grow with the next base joined to the preceding base having skipped at least one base in between. Some techniques are available to detect certain incorporation errors within a nucleic acid fragment, but these can be expensive and are not perfect and so a batch of single-stranded nucleic acid fragments may still include a reasonable proportion of errors.

Hence, in typical approaches to synthesis of double-stranded nucleic acids, a batch of different single-stranded nucleic acid fragments are placed in a common container and hybridised based on the matching overlap regions. However the presence of incorporation errors in the initial single-stranded nucleic acid fragments means that the yield of the eventual target double-stranded nucleic acid which is formed without errors can be relatively low. Typically, erroneous double-stranded portions of nucleic acid can be identified after the hybridisation process is complete. For example, this can be done using cloning, where a random selection from the manufactured batch of target double-stranded nucleic acid is made, and this sample is provided to a host (e.g. a bacterial host) which can then be used to generate multiple copies of the randomly selected sample. Sequencing can then be used to determine whether the selected sample was error-free. A number of parallel cloning lines may operate on different randomly selected batches from the manufactured sample of target double-stranded nucleic acid. Depending on the yield, a certain percentage of those cloning lines may then return a larger volume of error-free target double-stranded nucleic acid samples. However, a problem with this approach is that cloning is relatively expensive and slow, and the yields typically obtained using conventional techniques are so low that many cloning lines are needed in practice to provide sufficient chance that one of the cloning lines will generate error-free samples.

In practice, the rate of incorporation errors means that the maximum length (number of base-pairs) of double-stranded nucleic acid that can be synthesised artificially, rather than using hybridisation of cloned fragments generated using hosts, is relatively low and it has not yet been practical to synthesise gene-length sequences of double-stranded nucleic acid artificially. This is because the likelihood of errors scales with the length of the double-stranded nucleic acid according to a power law, so that the yield drops off greatly for longer target sequences.

At least some examples provide a method of providing one or more instances of a target double-stranded nucleic acid from a plurality of nucleic acid fragments, comprising:

a plurality of initial hybridisation steps, each initial hybridisation step comprising hybridising respective pairs of partially overlapping nucleic acid fragments to form a plurality of hybridised fragments; and one or more further hybridisation steps, each further hybridisation step comprising hybridising respective pairs of partially overlapping hybridised fragments which are the direct product of a corresponding pair of earlier hybridisation steps to form longer hybridised fragments, where each of the pair of earlier hybridisation steps comprises one of the initial hybridisation steps or one of the further hybridisation steps;

wherein said one or more further hybridisation steps comprise at least one further hybridisation step for which both of the corresponding pair of earlier hybridisation steps comprise an error-detecting type of hybridisation step;

the error-detecting type of hybridisation step comprising:
performing an error detecting operation to detect whether the hybridised fragments formed in the error-detecting type of hybridisation step comprise at least one erroneous hybridised fragment comprising at least one mismatching base pair in an overlap region hybridised in the error-detecting type of hybridisation step; and discarding at least part of said at least one erroneous fragment to exclude the at least one erroneous fragment from a subsequent further hybridisation step;

wherein the target double-stranded nucleic acid comprises a first strand of single-stranded nucleic acid hybridised to a second strand of single-stranded nucleic acid; and
in each hybridisation step, the hybridised fragment of nucleic acid formed in that hybridisation step is bound to a surface of a reaction site via the first strand or the second strand.

At least some examples provide a computer-readable program or data structure comprising instructions or control data for controlling an apparatus to perform the method described above. The computer program or data structure may be stored on a storage medium. The storage medium may be a non-transitory storage medium.

A sequence of hybridisations is provided comprising a number of initial hybridisation steps for hybridising nucleic acid fragments and one or more further hybridisation steps, where each further hybridisation step hybridises pairs of overlapping hybridised fragments which are the direct product of a corresponding pair of earlier hybridisation steps (which could be two earlier initial hybridisation steps, two earlier further hybridisation steps, or one earlier initial hybridisation step and one earlier further hybridisation step). Each further hybridisation step acts on the direct product of the pair of earlier hybridisation steps in the sense that it acts on the same molecules produced in the pair of earlier hybridisation steps, rather than, for example, on cloned molecules replicated by a bacterial host from molecules produced in the earlier hybridisation steps. Hence, the sequence of hybridisations can be done relatively fast.

For at least one further hybridisation step, both of the pair of earlier hybridisation steps which provide the fragments to be hybridised in that further hybridisation step, are error-detecting types of hybridisation steps. An error-detecting type of hybridisation step includes an error detecting operation for detecting whether the hybridised fragments formed in the error-detecting step include at least one erroneous fragment which has at least one mismatching base pair in the overlap region hybridised in that hybridisation step. If an erroneous fragment is detected, at least part of the erroneous fragment is discarded to exclude it from a subsequent further hybridisation step.

Hence, by ensuring that both of the earlier hybridisation steps which feed into a given further hybridisation step include error detection, more "good" fragments from one of the pair of earlier hybridisation steps are paired with "good" fragments from the other of the pair of earlier hybridisation steps. This reduces the wastage of "good" fragments by pairing them with an erroneous fragment, which is the main contributor to the extreme drop-off in yield at increasing lengths with existing techniques. The error detection operation can be performed while still performing the subsequent hybridisation on the direct product of the pair of earlier hybridisation steps, so there is no need to export the results of the earlier hybridisation steps, for example to a bacterial host, which would be slow and expensive, in order to perform error detection. By improving yield, an artificial synthesis of DNA or other double-stranded nucleic acid can be performed faster and more cost effectively in order to provide a given volume of the target double-stranded nucleic acid, than would be possible using existing techniques.

To enable the error detecting operation to be performed at the error-detecting type of hybridisation step and before the subsequent hybridisation step, so that the erroneous fragments can be excluded from that next hybridisation step, some degree of control over the order and timing of hybridisations of particular fragments may be needed. One approach for doing this could be to use manual or automated-controlled pipetting of samples from one container into another in order to control the sequence in which the fragments are brought together, and prevent fragments in different containers hybridising until the error detection has been performed on the fragments created in earlier hybridisations.

However, a faster and less labour-intensive approach may be to perform the method using an apparatus which has at least one lane of reaction sites aligned in a predetermined direction and a fluid control element to direct a flowing fluid over each reaction site in the predetermined direction. With such an apparatus the flowing fluid may be used to transport fragments from one reaction site to another. The apparatus may also include independently controlled "traps" (e.g. provided by static or oscillating electric fields, or magnetic fields in combination with ferrous beads) at each reaction site to facilitate the transport of fragments from one reaction site to another, thereby preventing loss of yield during the hybridisation steps. The reaction sites may comprise portions of a surface without a permanent physical barrier between the adjacent reaction sites (either there may be no physical barrier at all, or any physical barrier may be selectively removable), so that fragments can easily be transported from one site to another. The apparatus may further have temperature control circuitry to independently control a temperature at each reaction site. The temperature control can be useful for controlling the error detection steps, for example. With this approach, the order and timing with which respective portions of the target nucleic acid are hybridised can be carefully controlled, and so it becomes practical to perform error detection between successive hybridisation steps in a more cost effective manner.

In practice, to form a target double-stranded nucleic acid of a given length, a tree of hybridisations may be required, starting from initial single-stranded fragments or relatively small double-stranded fragments, and successively undergoing a number of hybridisations between the initial fragments or hybridised fragments formed in earlier hybridisations. The error-detecting type of hybridisation step may be provided at any of the hybridisation steps of the tree, e.g. at the initial hybridisation step, or at a further hybridisation step. In order to achieve some improvement in yield at a certain error rate, it is sufficient that there is just a single further hybridisation step for which both of the pair of earlier hybridisation steps feeding into that further hybridisation step are of the error-detecting type. However, a greater improvement in yield relative to pooled or sub-pooled approaches can be achieved by providing more than one further hybridisation step which acts on the direct product of a pair of error-detecting type of hybridisation steps. Each hybridisation step may hybridise fragments at a different overlap region of the target double-stranded nucleic acid, so the more hybridisation steps that are of the error-detecting type, the larger the fraction of the target nucleic acid that will be tested for errors and hence the greater the yield improvement. The greatest yield improvement can be achieved if every further hybridisation step acts on a pair of earlier hybridisation steps which are both of the error-detecting type, e.g. by ensuring that each initial hybridisation step and each further hybridisation step is of the error-detecting type. Nevertheless, in some cases a trade-off could be made between yield and performance, by accepting a lower yield in order to speed up the assembly process (as by omitting error detection steps, it may be possible to allow multiple hybridisation steps to be performed together at a single reaction site, reducing the number of separate transport events for transporting fragments from one site to another and reducing the delay in providing the control for as many error detection operations).

The error detecting operation may comprise weakening a bond between the partially overlapping fragments forming each erroneous hybridised fragment and providing fluid to wash away at least part of the at least one erroneous hybridised fragment. For example, one of the fragments in each hybridised pair may be fixed to a surface and so by weakening and/or breaking the bond between the fragments in erroneous hybridised fragments, and then passing the fluid over the fragments, this can efficiently wash away one of the pair of fragments which were hybridised to form the erroneous hybridised fragments, leaving the other fragment fixed to the surface. For the error-free fragments the bond may be weakened to a lesser extent or left intact by the error detecting step and so those fragments are not washed away as the bond is strong enough to maintain the pair of fragments bound together and attached the surface. This provides a fast and low cost mechanism of detecting and removing errors.

There may be different options for weakening the bond in erroneous fragments while leaving the remaining error-free fragments un-weakened or weakened to a lesser extent. In one example the error detecting operation may comprise adjusting a temperature of a reaction site on which the hybridised fragments are formed to a target temperature which corresponds to a margin below an expected melting temperature of the overlap region formed in the hybridisation step for an error-free hybridised fragment. This exploits the fact that in an erroneous hybridised fragment the melting temperature will typically be lower than if the hybridised fragment is error-free, because the overall bond between the hybridised fragments is weaker. The expected melt temperature of the overlap region can be predicted based on computer simulation and so by providing independently temperature controlled reaction sites and adjusting the temperature of a given site to a margin below the expected melting temperature for correct error-free fragments, this can enable sufficient weakening of the bonds only in the erroneous double-stranded fragments and not in the remaining error-free fragments, to enable separation of the erroneous hybridised fragments, and for example a subsequent flow of fluid over the fragments to wash away part of each erroneous double-stranded fragment. Even if this error detection mechanism is not 100% accurate this can still greatly improve yield while providing a cost effective means of error detection between successive hybridisations.

The partitioning of the target double-stranded nucleic acid into the single-stranded nucleic acid fragments may be selected so that, at each overlap region, a difference between the expected melting temperature of the overlap region in an error-free hybridised fragment and an expected melting temperature of the overlap region in an erroneous hybridised fragment with at least one base error within the overlap region is greater than a predetermined threshold. For example, computer simulations of the target nucleic acid may determine, based on the particular composition of bases at different points of the nucleic acid, which portions of the target are the preferred partition points at which the target should be split into nucleic acid fragments in order to maximise the expected difference between the melting temperatures between error-free and erroneous hybridised fragments, to increase the likelihood that the error detecting step can detect erroneous fragments and exclude them from subsequent hybridisations. More particularly, as different errors may lead to different overlap sequences, the partitioning may be performed to maximise the average difference in the expected melting temperature relative to an error-free hybridised fragment, with the average being evaluated across a number of candidate erroneous fragments with different types of error in the overlap region. For example, the predetermined threshold used may be at least 0.1° C.

The margin to which the temperature of the reaction site is set below the expected melting temperature for the error-free double-stranded fragment during the error detection step may, for example, not be the same as the threshold difference used to determine the partitioning. In some cases it can be useful to calculate bespoke temperature margins for each error-detecting type of hybridisation step. As each overlap region may comprise a different sequence of bases, the average temperature difference (across all potential erroneous fragments) between the melt temperature of a "good" fragment with perfectly matching bases in the overlap region and the melt temperature of an erroneous fragment with at least one incorrect base in the overlap region will vary depending on the composition of the overlap region. For those overlaps which have a larger average temperature difference, it can be useful to set the temperature margin for error detection larger than overlaps which have a smaller average temperature difference between "bad" and "good" fragments, as by increasing the temperature margin (i.e. setting the temperature of the reaction site lower relative to the expected melt temperature for error-free overlaps), the likelihood of some "good" fragments being rejected is reduced, increasing the ratio of the rejection of "bad" fragments to the rejection of "good" fragments caused by the error detection operation, and hence improving yield.

Alternatively, another way of detecting erroneous hybridised fragments may be to use one or more mismatching base pair detecting enzymes. Double-stranded nucleic acid with a mismatching base pair resulting from an imperfect hybridisation may be recognised and cleaved by one or more mismatching base pair detecting enzymes, examples of which include T7 endonuclease I, T4 endonuclease VII, *Escherichia coli* endonuclease V, CELI and CJE nucleases (Till, B. J. et al. (2004) Nucleic Acids Research 32: 2632-2641; Fuhrmann, M. et al. (2005) Nucleic Acids Research 33: e58). The products of the cleavage may dissociate, leaving single-stranded overhangs. Subsequently, these single-stranded overhangs may be degraded using a single-strand-specific exonuclease (e.g. *E. coli* exonuclease I) or a proofreading DNA polymerase.

As mentioned above, the hybridised fragments may be transported between reaction sites on which respective hybridisation steps are performed, by transport in a flowing fluid. This can be more efficient than manual or automated pipetting from container to container, and also enables the transport of hybridised fragments to be performed using the same fluid flow mechanism used to discard erroneous fragments during the error detection. When fragments are released from one site and transported in the flowing fluid to a next reaction site, a barrier may be provided to prevent these released fragments flowing beyond the next reaction site. For example, the barrier could be provided by electric or magnetic fields or field gradients (electric or magnetic traps), or by physical means such as selectively introducing a sluice barrier.

The target double-stranded nucleic acid may comprise a first strand of single-stranded nucleic acid hybridised to a second strand of single-stranded nucleic acid. Each of the first and second strands may be partitioned into the initial (single-stranded or double-stranded) fragments which are used to form the target double-stranded nucleic acid. In order to support the use of fluid to control transport and error detection as discussed above, in each hybridisation step, the double-stranded fragment of nucleic acid formed in that hybridisation step may be bound to a surface of a reaction site via either the first strand or the second strand. The binding may occur either at the 5' or the 3' end of either the first strand or the second strand. The binding may be strong enough to withstand the force provided by the flowing fluid, unless the binding is selectively detached (as discussed in more detail below). This means that when the hybridised fragments are bound to the surface, and the error detection operation weakens the bond at the overlap region, washing fluid over the fragments may wash away part of the erroneous fragments where the bond has been sufficiently weakened, but remaining "good" fragments stay intact and bound to the surface.

However, if the fragments of nucleic acid formed in each hybridisation step are always bound to the reaction site via the same one of the first strands and the second strand of the target, then this may mean that even if an erroneous fragment is detected at one hybridisation step, it may still hybridise with a "good" fragment at the next hybridisation step and so waste the "good" fragment and reduce yield even though the error was detected. This is a consequence of the fact that when errors are detected and eliminated by discarding part of a fragment bound to the surface whose bond has been weakened, only the "loose" portion (the portion not directly bound to the surface) of the weakened hybridised fragment can be discarded, and the "bound" portion (the portion directly bound to the surface) will still remain fixed to the surface of the reaction site, and so when the remaining fragments are released to transport to the reaction site for a next hybridisation step, the "bound" portion of erroneous fragments is still present and so could bond with other fragments if a matching overlap region is present and exposed. If the same strand was fixed to the reaction site at each hybridisation step, then the overlap region exposed at the next hybridisation would correspond to the "bound" portion of the previous hybridisation, so that it would be possible for "orphaned" fragments on the bound side of a previously detected erroneous fragment to hybridise with "good" fragment at the next hybridisation, and hence reduce yield. The "bound" and "loose" portions could be single-stranded fragments of nucleic acid or double-stranded fragments of nucleic acid, depending on which fragments are being hybridised in the hybridisation step at which the error detection is performed.

This issue can be addressed by instead ensuring that a given hybridisation step, which is performed at a given reaction site and acts on products of a pair of earlier hybridisation steps which are both of the error detecting type, comprises hybridising first hybridised fragments which are bound to the surface of the given reaction site via one of the first and second strands, and second hybridised fragments formed at an earlier reaction site in an earlier hybridisation step when bound to the surface of the earlier reaction site via the other of the first and second strands. This effectively alternates, between successive hybridisation steps, which of the first and second strands of the target is bound to the reaction site. This means that the overlap region hybridised at the next hybridisation corresponds to the "loose" portion of the hybridised fragment formed at the previous hybridisation step, so that if an error has been detected and the loose side of an erroneous fragment has been discarded, the subsequent hybridisation cannot take place as the remaining "bound" portion of the erroneous fragment does not have an overlap region which matches the overlap region exposed at the next hybridisation.

If not all the hybridisation steps are of the error-detecting type, it is not essential for every pair of successive hybridisation steps to alternate which strand is bound to the reaction site between the hybridisation steps. However, in order to support a greater number of error-detecting steps, it can be useful to alternate which of the first and second strands is bound to the reaction site at every transition from one hybridisation step to another. Hence, the initial hybridisation steps and the at least one further hybridisation step may form a sequence of hybridisation steps in which for any pair of hybridisation steps in which the second hybridisation step of the pair hybridises a hybridised fragment formed in the first hybridisation step of the pair with a further fragment, the hybridised fragments formed in the pair of hybridisation steps are bound to a surface of a corresponding reaction site via opposite ones of the first strand and the second strand respectively. This approach increases the opportunity to discard erroneous fragments and avoid them hybridising with "good" fragments, and hence improves yield. The control over which strand is bound to the surface at each hybridisation steps may be done by controlling the initial arrangement of the initial fragments on each reaction site and the sequence in which combinations of hybridised fragments are brought together.

In at least one of said error-detecting type of hybridisation step, remaining hybridised fragments following the error detection operation may be selectively detached from a surface of a reaction site. At least some of the fragments at another reaction site may remain attached to the other reaction site. It is not necessary to perform the selective detaching for every error-detecting type of hybridisation step, because for some hybridisation steps the next hybridisation step may be performed at the same site as the previous hybridisation step (with the product of another hybridisation step being transported to the same site), so that sometimes the remaining hybridised fragments may remain fixed to await the arrival of the next batch of fragments for the next hybridisation step.

Also, it is not necessary for the accuracy of the selective detachment to be 100% perfect. A detachment mechanism for detaching fragments from a target reaction site may be used which allows some remaining fragments which do not contain errors in the relevant overlap region to remain attached to the target reaction site, or which allows some fragments at a reaction site other than the target reaction site to be detached. The losses incurred by such incorrect detachment may be less significant than the improvement in yield relative to pooled or sub-pooled approaches provided by the error detection, so that overall the yield may still be improved even with some losses caused by incorrect detachment. Hence, it may be enough to provide a detachment mechanism for which the probability of detachment from a target reaction site is higher than the probability of detachment from other non-targeted reaction sites, even if not all fragments detach from the target reaction site or some fragments detach from a non-targeted reaction site. In any case, a way to impede these losses caused by incorrect detachment may be to make use of electric or magnetic traps at each reaction sites during the detachment steps.

The detachment mechanism can be implemented in different ways. In some examples, a cleavable linker substance could be used to attach the fragments to the corresponding reaction sites, which could be arranged to detach the fragment from the reaction site when subject to a certain chemical reagent. Examples of cleavable linker substances include a chemical composition having a succinate moiety bound to a nucleotide moiety, for example such that cleavage produces a 3' hydroxy nucleotide. More particularly, the cleavable linker may be one of 5'-dimethoxytrityl-thymidine-3'-succinate, 4-N-benzoyl-5'-dimethoxytrityl-deoxycytidine-3'-succinate, 1-N-benzoyl-5'-dimethoxytrityl-deoxyadenosine-3'-succinate, 2-N-isobutyryl-5'-dimethoxytrityl-deoxyguanosone-3'-succinate, or combinations thereof.

Fragments may also be detached enzymatically, for example through the use of specific recognition sequences flanking the nucleic acid to be detached, which are recognisable by enzymes such as restriction endonucleases. The choice of restriction endonuclease cleavable site and the enzyme itself can depend on desired properties of the cleavage product. For example, certain restriction endonucleases produce "blunt" ends, whilst others produce "overhangs" of nucleic acid. In one embodiment, the restriction endonuclease is a class II restriction endonuclease. Example type II restriction endonucleases that cleave nucleic acids (e.g. DNA) within their recognition sequence and produce blunt-ended products include AluI, EcoRV, HaeIII, PvuII and SmaI. HaeIII may also cleave single-stranded nucleic acids. Examples of type II restriction endonucleases that cleave nucleic acids (e.g. DNA) within their recognition sequence and produce overhang-ended products include BamHI, EcoRI, NotI and XbaI. In another embodiment, the restriction endonuclease is a class IIS enzyme. Such class IIS enzymes cleave a nucleic acid externally to their recognition sequence. Example class IIS restriction endonucleases include MlyI, BspMI, BmrI, BtsI and FokI. In another preferred embodiment, a uracil-DNA glycosylase (UDG) and a apurinic/apyrimidinic (AP) site endonuclease are used for the detaching of fragments. The recognition sequence may contain at least one uridine. Treatment with UDG generates an abasic site. Treatment on an appropriate substrate with an apurinic/apyrimidinic (AP) site endonuclease will then cleave the nucleic acid strand.

In some examples, the detaching mechanism may target specific sites by providing a physical means of preventing certain sites being affected by the detaching mechanism. For example, in embodiments where each reaction site corresponds to a physically separated container, vessel or well, the reagents for breaking down the linker substance or the enzymes could be applied only to the target reaction sites and not to other sites. Alternatively, supply channels with control valves could be used to direct reagents or enzymes onto particular sites. Another approach may be to use a temperature-activated release mechanism. For example, in some examples the selective detaching may comprise heating the reaction site to a predetermined detaching temperature of a linker substance binding the remaining hybridised fragments to the reaction site, where the linker substance is arranged to detach from the surface when at the predetermined detaching temperature. Alternatively, the selected detaching may comprise exposing the remaining hybridised fragments to a detaching enzyme, for example a temperature-activated detaching enzyme, and adjusting a temperature of the reaction site to an activation temperature of the detaching enzyme. The use of the electric or magnetic traps can also be used during the detachment process to improve yield. These traps enable the complementary nucleic acid fragment pairs to be kept close to each other in case they melt due to the detaching temperature required. By holding the pairs at the reaction site using the traps, then even if some pairs separate during the detachment process, this gives the pairs an opportunity to re-anneal again when the temperature is lowered before the traps are released to enable transportation of the fragments to the subsequent reaction site. Regardless of the particular manner in which the detaching mechanism is implemented, by providing a mechanism for selecting when fragments are released from one site so that they can be transported to another, this provides control over the order and timing at which successive hybridisations of fragments are performed, enabling fragments to be detached at one reaction site while other fragments remain attached at another reaction site, so that further hybridisation steps can be deferred until the error detection has been performed between successive hybridisations.

Other than a hybridisation step performed on pairs of single-stranded fragments, each hybridisation step may comprise a ligation operation performed on the hybridised fragments formed in that hybridisation step. For an error-detecting type of hybridisation step, the ligation operation is performed on the remaining hybridised fragments excluding the at least one erroneous fragment detected in the error detection operation. Hence, the remaining double-stranded fragments which remain at a given site following the error detection may be subjected to a ligation enzyme which ligates gaps in the nucleic acid backbone, effectively joining the fragments together. This may have the effect of increasing the strength of the bond between the respective strands before the fragments are forwarded to the next hybridisation step, so that even if in a subsequent hybridisation or error detection step the temperature of a reaction site is adjusted to a melt temperature of a previously hybridised overlap region, the ligation step performed previously prevents the strands hybridised in the previous hybridisation step from separating. The ligation operation avoids the need for ever-increasing precision in the temperature control needed to detect a single base error in the error detection operation as the fragment length increases. This is because performing ligation of the backbone at the boundary of the recently hybridised overlap region increases the length of the portion of the fragment along which the nucleic acid backbone is continuous with no gaps, so that a higher melt temperature would be required for the two strands to separate along the portion having the continuous backbone. Hence, this means that the melt temperatures needed for testing the strength of the bond at other overlap regions in subsequent hybridisation steps can be significantly lower than the melt temperature which would be needed for the already hybridised sections of the nucleic acid to dissociate, so that subsequent error detection steps do not affect portions of the fragment corresponding to already tested overlap regions. The ligation step is not needed for hybridisation steps acting on pairs of single-stranded fragments, as in this case the nucleic acid backbone is already completely ligated along the full length of the fragment (it is only steps which ligate a double-stranded fragment with sticky ends with a further single-stranded or double-stranded fragment which have a gap in the backbone and so can be subject to ligation).

The ligation operation may be performed using a suitable ligase, such as T4 DNA ligase or topoisomerase. Nucleic acids to be ligated should preferably be phosphorylated at the 5' end. Such phosphorylation may be performed using a suitable kinase, such as T4 polynucleotide kinase. The kinase may be used before the ligase, or a combination of both kinase and ligase may be used.

In some examples, the initial batch of nucleic acid fragments may comprise single-stranded nucleic acid fragments. Hence, the initial hybridisation steps may comprise single-strand hybridisations to form double-stranded fragments. In this case, each of the initial batch of nucleic acid fragments may comprise at least one overlap region for overlapping with a corresponding overlap region of another of the nucleic acid fragments, and each base of the target double-stranded nucleic acid (in both the first strand and the second strand) may be within one of the overlap regions of one of the nucleic acid fragments. Hence, this means that each base will be within an overlap region for at least one hybridisation step and so if error detection is performed at each hybridisation then each base is tested for errors and so this increases the percentage of errors that can be detected.

Alternatively, the initial hybridisation steps could be performed on partially-overlapping double-stranded fragments of nucleic acid (with sticky ends or overhangs, i.e. regions of single-stranded nucleic acid protruding beyond the end of the double-stranded portion of the fragment, where the overlap region will be hybridised with an overlap region of another fragment), so that there are already some portions of each fragment in the initial batch where the bases in an intermediate part of the fragment already have their complementary base on the other strand. In this case, not all the bases of the target double-stranded nucleic acid will be within one of the overlap regions of the initial batch of fragments, and so this may reduce the extent to which errors can be detected.

The initial batch of nucleic acid fragments may be formed on the same apparatus as the apparatus used to perform the hybridisation steps prior to performing the initial hybridisation steps. For example, a number of single-stranded nucleic acid fragments (e.g. oligonucleotides) may be grown on the reaction sites, and some of those reactions sites may then also be used for performing subsequent hybridisation steps. The fluid transporting mechanism and temperature-controlled release mechanism may be used to control which nucleic acid fragments are hybridised together in the sequence of hybridisation steps. Alternatively, in other approaches some pre-assembled initial fragments may be formed separately, and attached to the surface of the hybridisation sites before then performing the sequence of hybridisation steps.

A computer program or a computer-readable data structure may be provided which comprises instructions or control data for controlling an apparatus to perform the method discussed above. For example, the program or data structure may specify the timings and levels at which temperatures at the respective reaction sites are to be adjusted, in order to control the error detection and flow. Hence, different computer programs or data structures may be provided corresponding to specific target nucleic acid samples, providing the specific control data for assembling that particular target.

Nucleic Acids

The methods of the invention enable the creation of nucleic acids, such as genes, genomes and chromosomes starting from information only, i.e. the invention may provide nucleic acids without a requirement for existing nucleic acid molecules, such as genes or genomes.

The methods of the invention are not particularly limited to the type of nucleic acid to be provided. For example, the nucleic acid may be a deoxyribonucleic acid (DNA), ribonucleic acid (RNA) or xeno nucleic acid (XNA).

In one embodiment, the nucleic acid is a DNA. In one embodiment, the nucleic acid is a RNA. In one embodiment, the nucleic acid is a XNA. Xeno nucleic acid (XNA) is a synthetic nucleic acid that is an artificial alternative to DNA and RNA. As with DNA and RNA, XNA is an information-storing polymer, however XNA differs to DNA and RNA in the structure of the sugar-phosphate backbone. By 2011, at least six synthetic sugars had been used to create XNA backbones that are capable of storing and retrieving genetic information. Substitution of the backbone sugars make XNAs functionally and structurally analogous to DNA and RNA.

The term "oligonucleotide" as used herein may refer to short nucleic acid polymers, for example polymers of DNA, RNA or XNA nucleotides. Although the exact length of an oligonucleotide is not particularly limited, an oligonucleotide may be, for example, about 4-200 nucleotides in length.

The term "polynucleotide" as used herein may refer to longer nucleic acid polymers, for example polymers of DNA, RNA or XNA nucleotides.

The term "nucleotide" as used herein may refer to nucleotides, such as DNA and RNA nucleotides, as well as nucleotide analogues.

The term "hybridisation" as used herein refers to the hydrogen bonding of opposing nucleic acid strands, preferably Watson-Crick hydrogen bonding between complementary nucleoside or nucleotide bases.

Nucleotides each comprise a nucleobase. The term "nucleobase" or "base" as used herein refers to nitrogenous bases, including purines and pyrimidines, such as the DNA nucleobases A, T, G and C, the RNA nucleobases A, U, C and G, as well as non-DNA/RNA nucleobases, such as 5-methylcytosine ($^{Me}C$), isocytosine, pseudoisocytosine, 5-bromouracil, 5-propynyluracil, 5-propyny-6-fluorouracil, 5-methylthiazoleuracil, 6-aminopurine, 2-aminopurine, inosine, 2,6-diaminopurine, 7-propyne-7-deazaadenine, 7-propyne-7-deazaguanine and 2-chloro-6-aminopurine.

Nucleic acids may be, for example, single- or double-stranded.

The "sense" strand ("positive" or "coding" strand) has the same sequence as the messenger RNA into which the double-stranded polynucleotide is transcribed (with the exception of any typical nucleobases differences, e.g. between DNA and RNA, T is replaced by U). The opposite, "anti-sense" strand ("negative" or "anticoding" strand) is used as the template for messenger RNA during transcription. The anti-sense strand is thus responsible for the RNA that may be, for example, translated to protein, while the sense strand possesses a nearly identical makeup to that of the messenger RNA.

Complementarity is the principle affecting the binding of two single-stranded nucleic acids to form a double-stranded nucleic acid. It is a property shared between two nucleic acid sequences, such that when they are aligned antiparallel to each other, the nucleotides opposing each other in the two sequences will all be complementary for optimal binding. At the molecular level, complementarity is determined by optimal hydrogen bonding between specific base pairs. For example, in DNA, adenine is complementary to thymine, and guanine is complementary to cytosine; and in RNA, adenine is complementary to uracil, and guanine is complementary to cytosine. Complementary pairing of bases allows information to be copied from one molecule to another, and, in nature, from one generation of cells to another. Lack of complementarity at a base pair of a double-stranded nucleic acid may be referred to as a "mismatch".

A double-stranded nucleic acid may be comprised of two strands of the same length, in which case both ends of the double-stranded nucleic acid may be blunt ended.

Alternatively, one or both ends of a double-stranded nucleic acid may exhibit an overhang of single-stranded nucleic acid, for example if one strand is longer than the other or if the two strands are offset from one another (such overhangs may be referred to as "sticky ends"). Such overhangs may enable a single-stranded nucleic acid or double-stranded nucleic acid to bind to two or more complementary nucleic acids, and thus, by the same token, the double-stranded nucleic acid may bind to one or more further single-stranded or double-stranded nucleic acids by virtue of base pairing with the overhang, thus creating regions of overlap between opposing single-stranded nucleic acids.

These concepts are illustrated by way of example only in FIG. 1, which depicts an example double-stranded DNA comprised of 10 oligonucleotides. Each strand is comprised of a number of separate oligonucleotides, which are represented in the figure by differing text formats (plain text, underline, bold and/or italic). The top (sense) strand is comprised of 5 oligonucleotides (A1-A5) and the bottom (antisense) strand is comprised of 5 oligonucleotides (B1-B5). It is not essential for the sense and antisense strands to comprise the same number of oligonucleotides. In this example, the top and bottom strands are complementary and, for example, oligonucleotide A2 overlaps with oligonucleotides B3 and B4, having regions of complementarity with each of B3 and B4.

Melting Temperature ($T_m$)

The melting temperature ($T_m$) of a nucleic acid sequence is the temperature at which 50% of the nucleic acid and its complement are in duplex form.

The melting temperature of a nucleic acid sequence may be determined empirically. For example, a single-stranded nucleic acid and its complement may be introduced into a cell in a temperature-controlled UV spectrophotometer. Variation in UV absorbance at a suitable wavelength (e.g. 260 nm) may then be measured as a function of temperature, which will typically give rise to an S-shaped curve with two plateaus. The melting temperature may then be determined as the temperature at the point on the melting curve that is half-way between the two plateaus.

Although empirical means may be an accurate manner of determining melting temperatures, these experiments are typically time-consuming. Alternatively, melting temperatures may be calculated using any of a number of formulae that have been developed for this purpose and the skilled person will be readily able to select a suitable method.

A number of formulae have been developed that enable calculation of melting temperatures based solely on nucleotide content of a nucleic acid sequence. By way of example, the following formula may be used to calculate the melting temperature of a nucleic acid:

$$T_m = 4 \times (G+C) + 2 \times (A+T)$$

where: G, C, A and T are the number of occurrences of each nucleotide.

An alternative example formula for calculating the melting temperature of a nucleic acid is:

$$T_m = 64.9 + \frac{41 \times (G + C - 16.4)}{(A + T + G + C)}$$

where: G, C, A and T are the number of occurrences of each nucleotide.

Factors other than nucleotide content may affect the melting temperature of a nucleic acid in solution, such as nucleic acid strand concentration, salt concentration and the concentration of any denaturants, such as formamide or DMSO. Further formulae have been developed which take account of such factors. By way of example, the following formula, which comprises a salt concentration adjustment, may be used to calculate the melting temperature of a nucleic acid:

$$T_m = 4 \times (G+C) + 2 \times (A+T) - 16.6 \times \log_{10} 0.050 + 16.6 \times \log_{10}[\text{Na}^+]$$

where: G, C, A and T are the number of occurrences of each nucleotide.

An alternative example formula, which comprises a salt concentration adjustment, for calculating the melting temperature of a nucleic acid is:

$$T_m = 100.5 + \left( \frac{41 \times (G + C)}{(A + T + G + C)} \right) - \left( \frac{820}{(A + T + G + C)} \right) + 16.6 \times \log_{10}[\text{Na}^+]$$

where: G, C, A and T are the number of occurrences of each nucleotide.

Although these example formulae refer to DNA bases, similar formulae may be equally applicable to other nucleic acids, such as RNA.

Other approaches may be based on the use of thermodynamic calculations to determine melting temperatures. From observation of melting temperatures it is possible to experimentally determine the associated thermodynamic parameters ($\Delta G$, $\Delta H$ and $\Delta S$) for nucleic acid sequences and, vice versa, when the thermodynamic parameters of a given nucleic acid sequence are known it is possible to predict the melting temperature of the sequence.

The nearest-neighbour model provides an accurate means for determining the thermodynamic parameters for a given nucleic acid sequence and therefore can be used to predict melting temperatures. This model is based on the understanding that the interaction between bases on different strands may also depend on the neighbouring bases. For example, instead of treating a nucleic acid duplex as a number of interactions between base pairs, the nearest-neighbour model treats the duplex as a number of interactions between "neighbouring" base pairs. Empirically determined thermodynamic basis sets for all possible nearest neighbour interactions (e.g. for DNA, see Breslauer, K. J. et al. (1986) Proc. Natl. Acad. Sci. USA 83: 3746-3750; and for RNA, see Freier, S. M. et al. (1986) Proc. Natl. Acad. Sci. USA 83: 9373-9377) may thus be used to calculate the thermodynamic parameters for a specific sequence and hence predict the melting temperature of that sequence.

Preparation of Oligonucleotides

Oligonucleotides may be prepared, for example, using solution- or solid-phase approaches.

Oligonucleotides can be synthesised, for example, either chemically (e.g. using phosphoramidite coupling chemistry (Beaucage et al. (1981) Tetrahedron Lett. 22: 1859; Beaucage et al. (1992) Tetrahedron 48: 2223-2311)) or enzymatically.

High throughput oligonucleotide synthesis can be achieved using an automated synthesiser.

Phosphoramidite-based synthesis of oligonucleotides involves activation of nucleoside phosphoramidite monomer precursors by reaction with an activating agent to form activated intermediates, followed by sequential addition of the activated intermediates to the growing oligonucleotide chain to form the oligonucleotide product. The oligonucleotide chain is typically anchored at one end to a suitable solid support.

The terminal protecting group (e.g. 5'-DMT) may be retained or removed depending on the subsequent purification method. The oligonucleotide may then be cleaved from the solid support prior to purification, typically by treatment with ammonium hydroxide, which also serves to remove base and phosphate triester protecting groups.

Example enzymatic methods include the "uncontrolled" coupling and "controlled" coupling methods described herein.

The "uncontrolled" method may use a polymerase, such as a template-independent polymerase or a nucleotidyl transferase to add a desired nucleotide to extend an existing oligonucleotide. The product of each extension step is a mixture of oligonucleotides in which different numbers of the nucleotide have been added (i.e. [starting oligonucleotide]+(n) nucleotides, wherein n=0, 1, 2, 3 etc.). The desired extension product may then be purified from the reagents and side-products. Nucleotidyl transferase incubation and oligonucleotide purification steps may be repeated until the final oligonucleotide is reached. Example of nucleotidyl transferases include polynucleotide phosphorylase (Shum et al. (1978) Nucleic Acids Res. 5: 2297-2311) and terminal deoxynucleotidyl transferase (Schott et al. (1984) Eur. J. Biochem. 143: 613-620).

The "controlled" method is an adaptation of this, in which the nucleotide reagent used in the extension step is blocked to prevent addition of more than one nucleotide during the enzymatic extension step. This "controlled" method might need an engineered modified template-independent polymerase to be able to incorporate these blocked nucleotides. After the extension step, the blocking group is removed to enable the addition of the subsequent blocked nucleotide.

Further aspects, features and advantages of the present technique will be apparent from the following description of examples, which is to be read in conjunction with the accompanying drawings, in which:

FIG. 1 illustrates an example of a target DNA sequence (A=SEQ ID NO: 1) partitioned into single-stranded fragments;

FIG. 2 illustrates pooling and sub-pooling;

Figure 6:
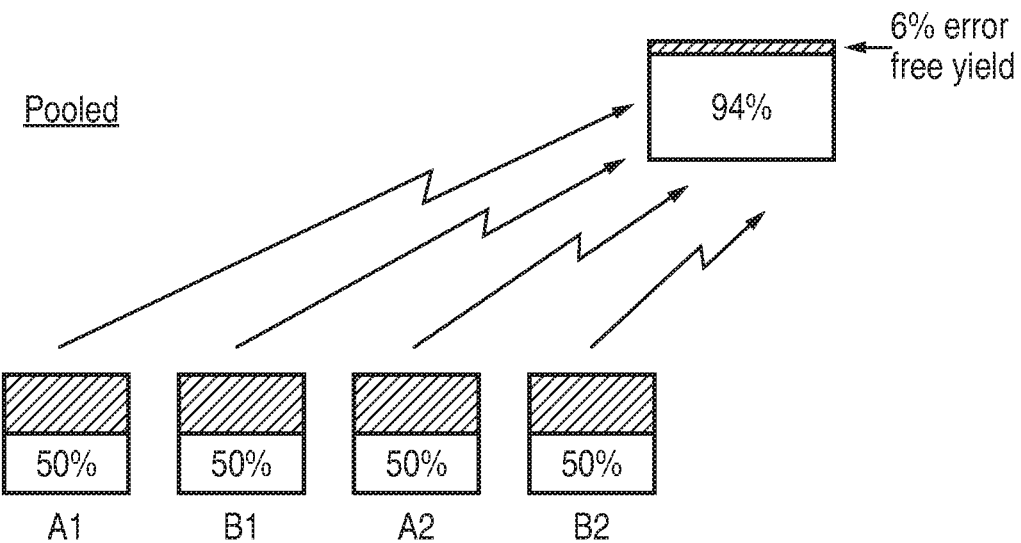
Figure 7:
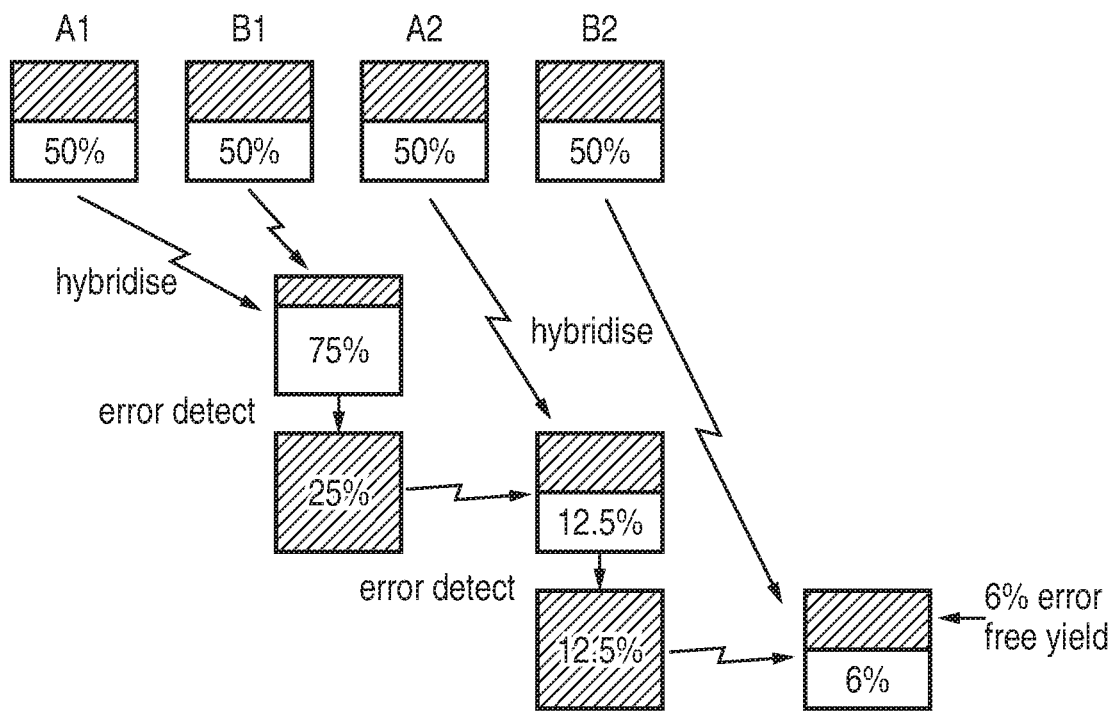
Figure 8:
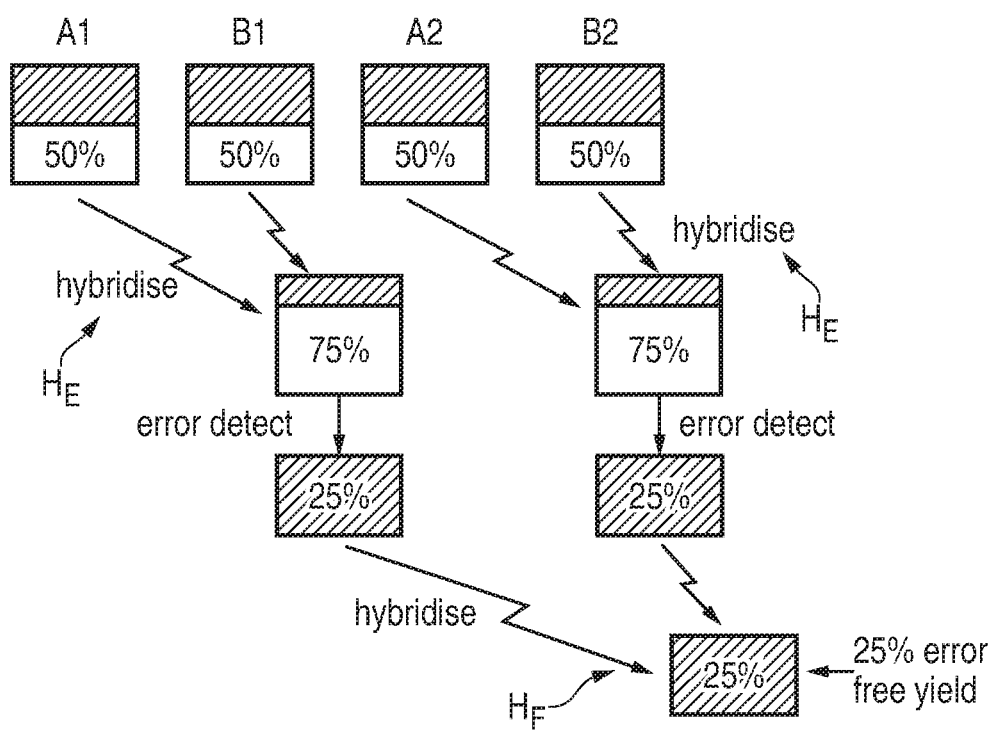
Figure 9:
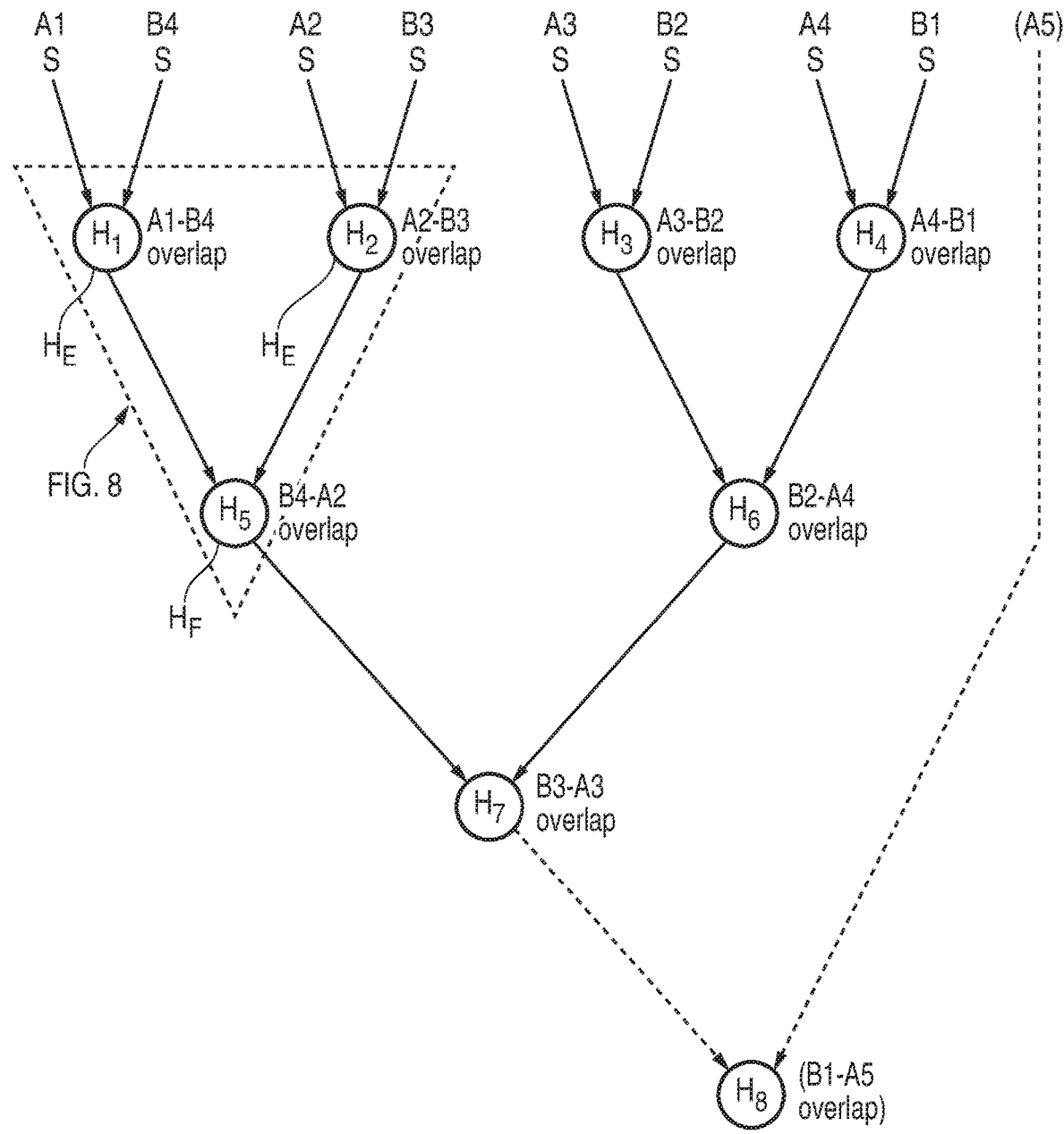
Figure 10:
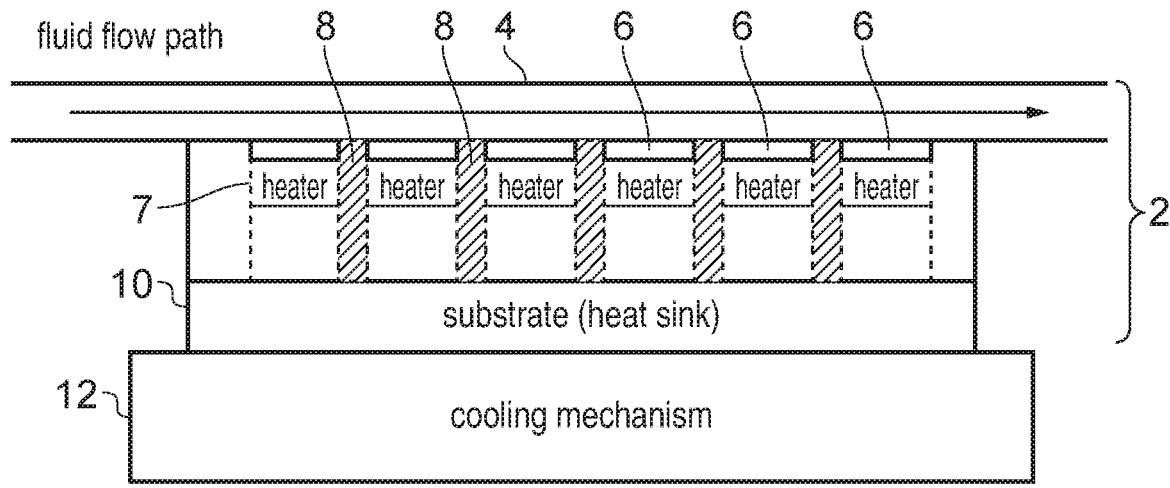
Figure 11:
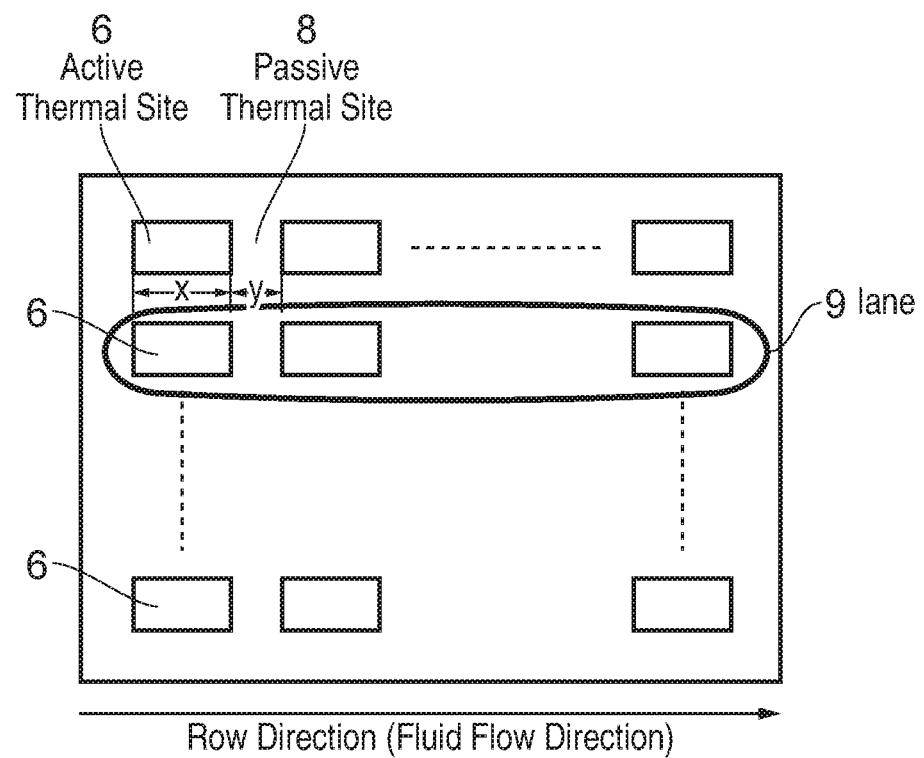
Figure 12:
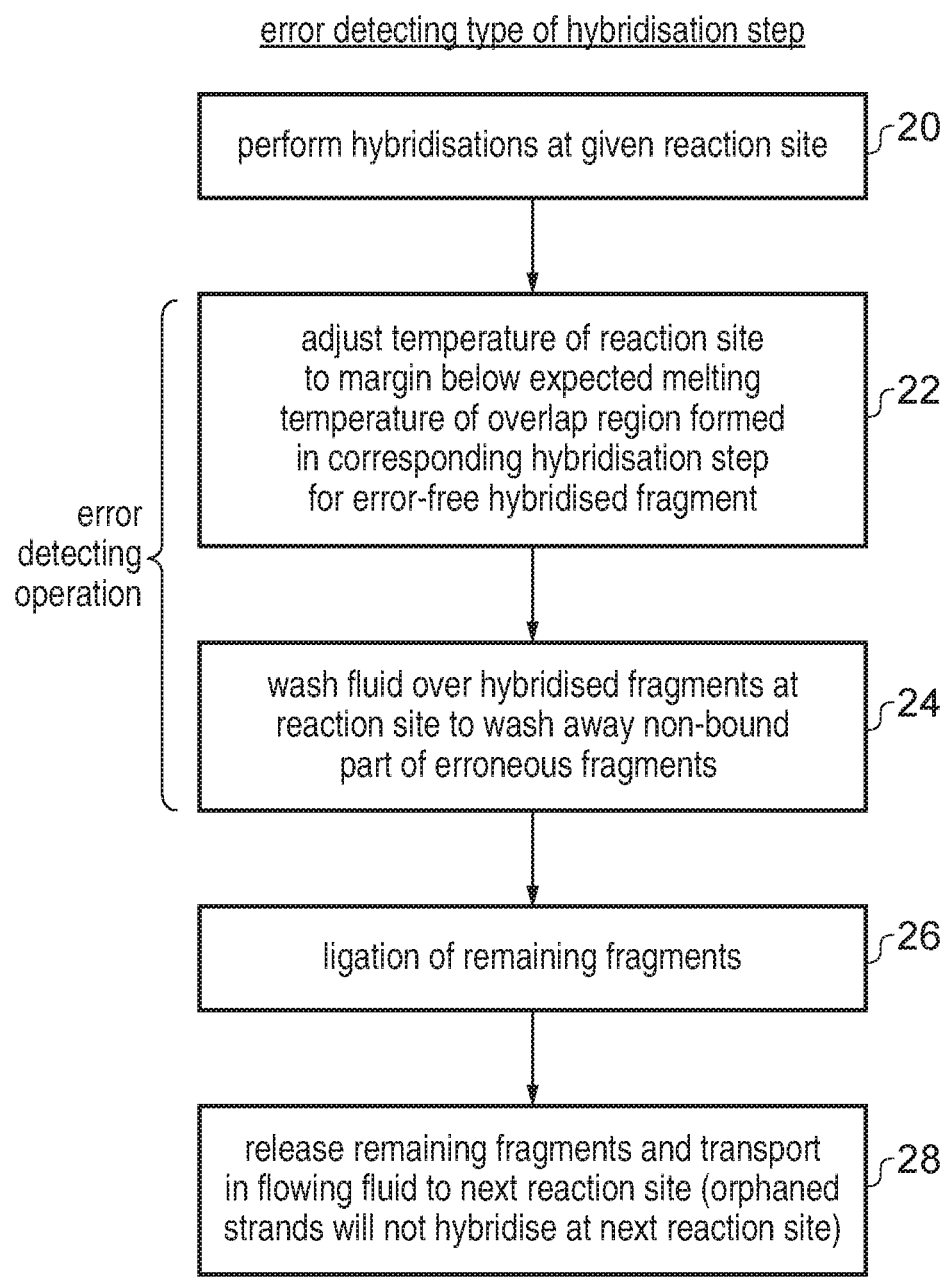
Figure 15:
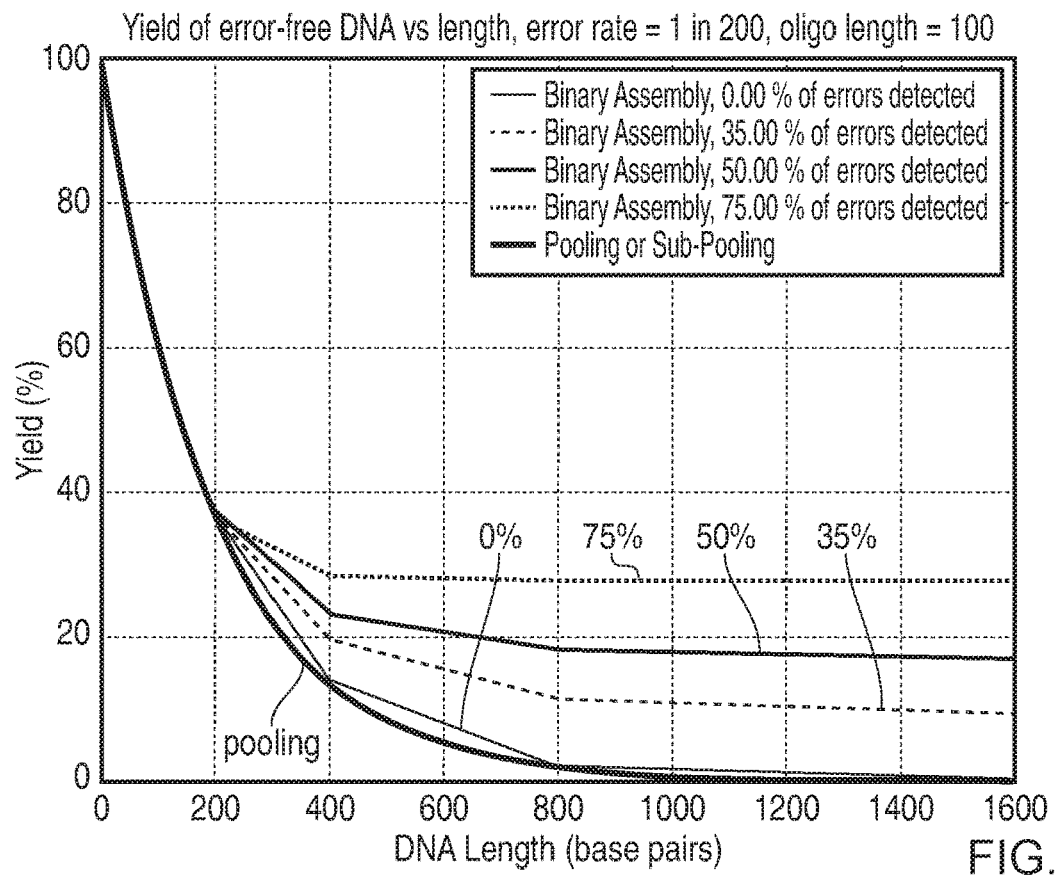
Figure 16:
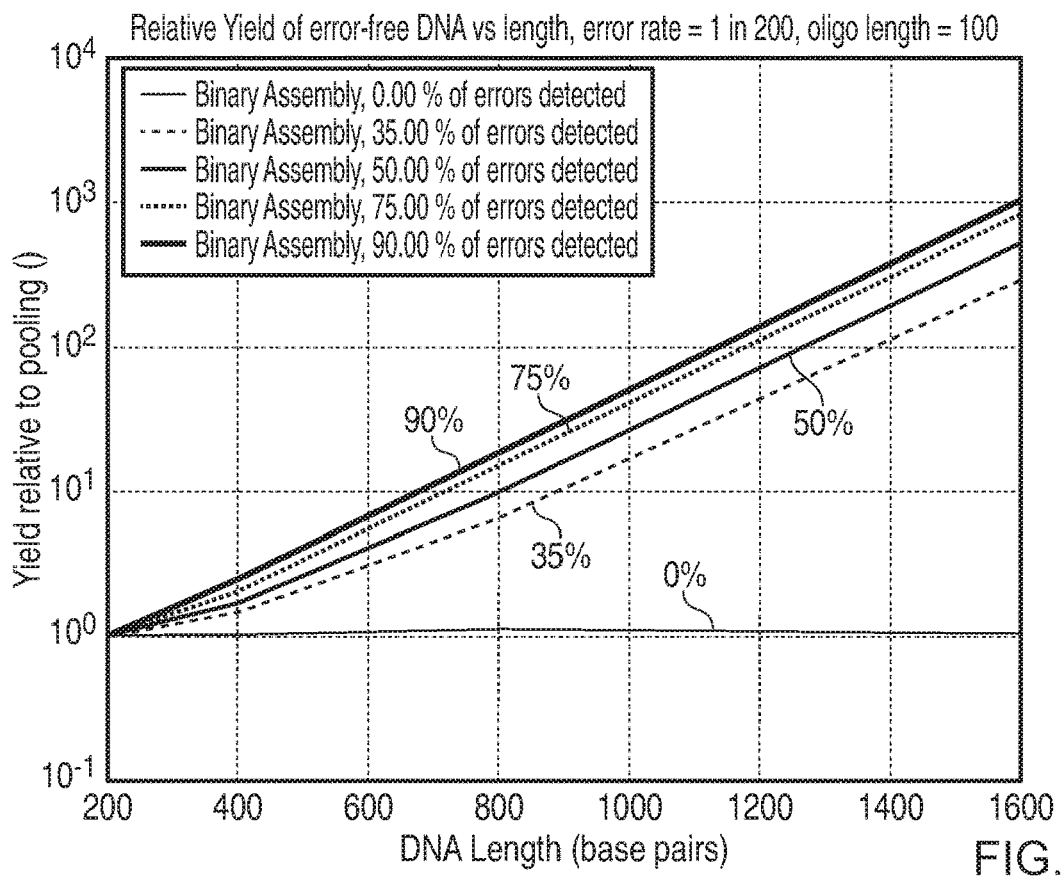
Figure 17:
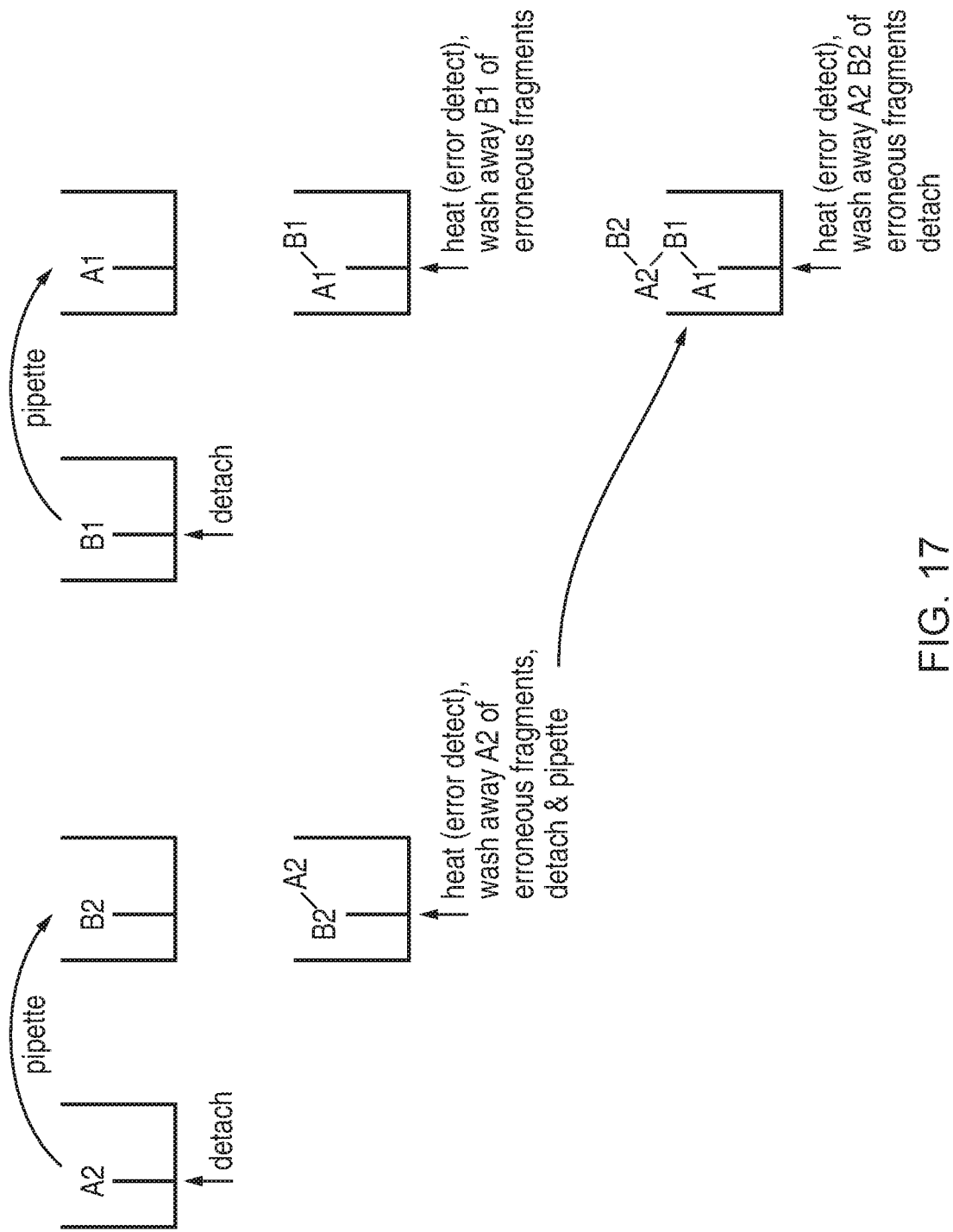
Figure 19:
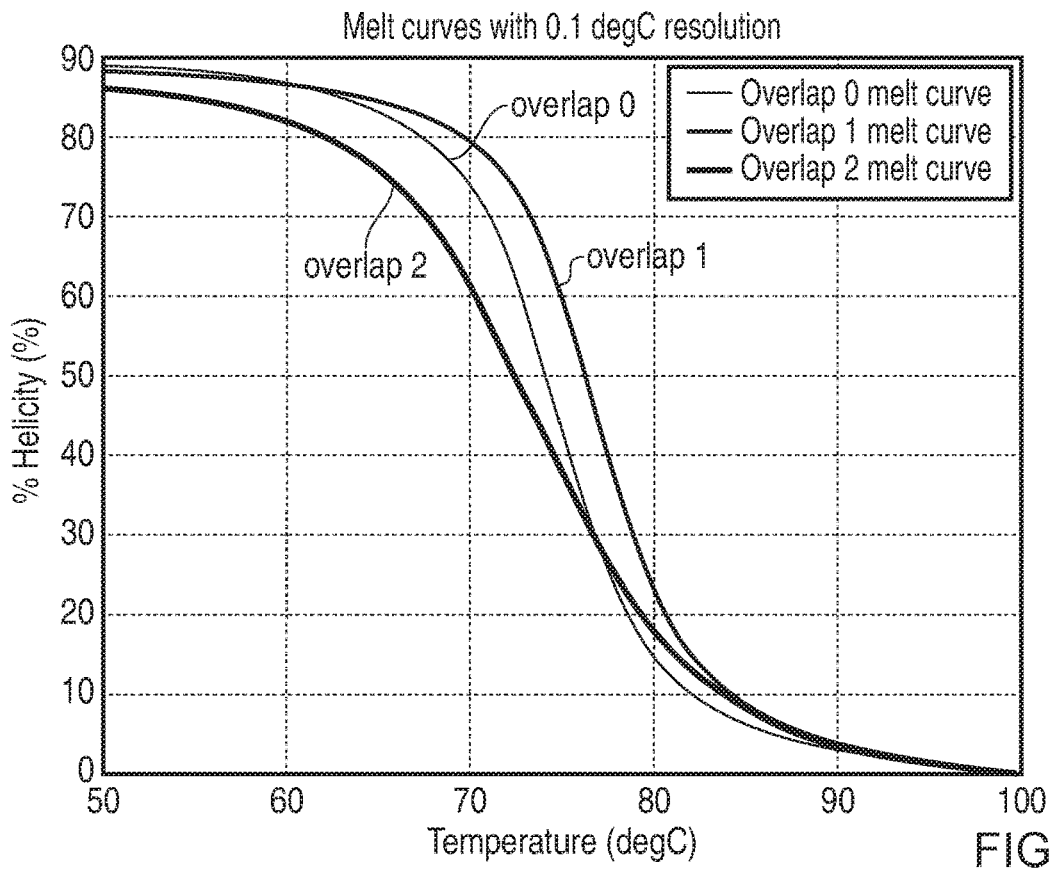
Figure 20:
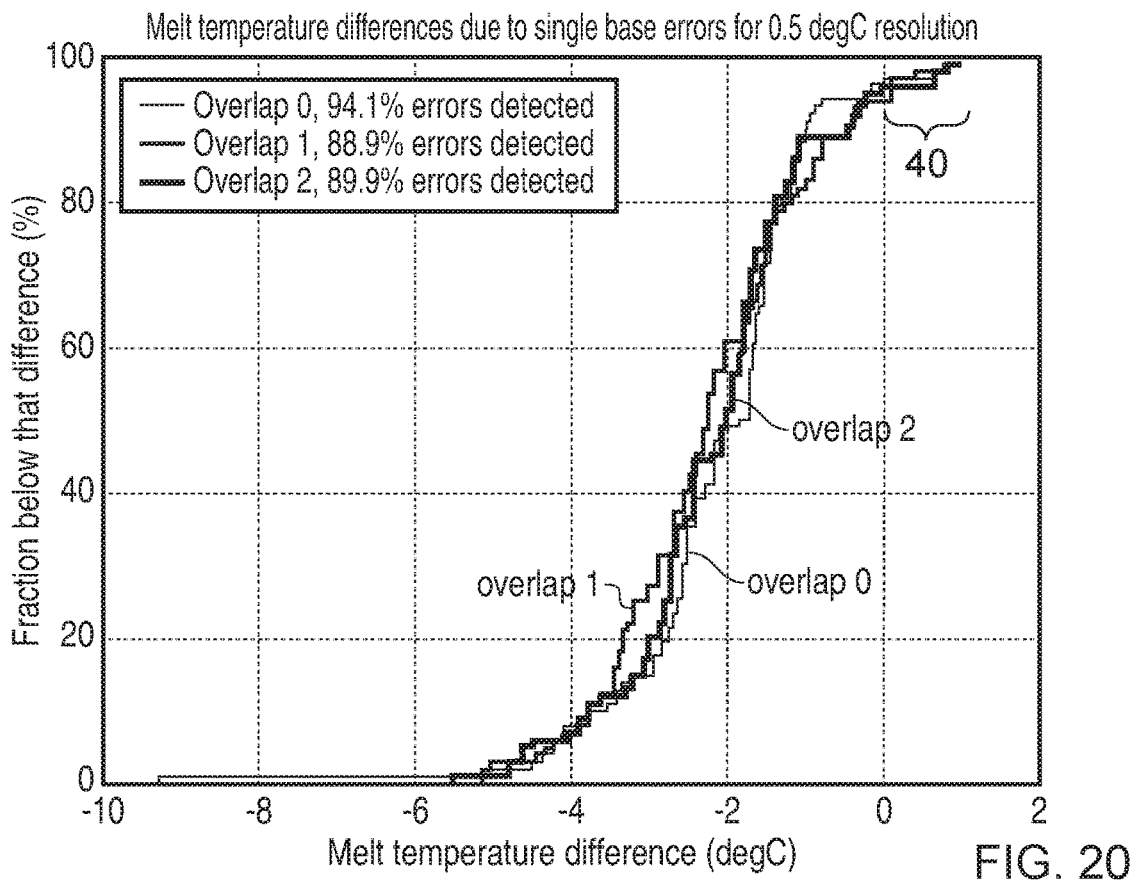
Figure 21:
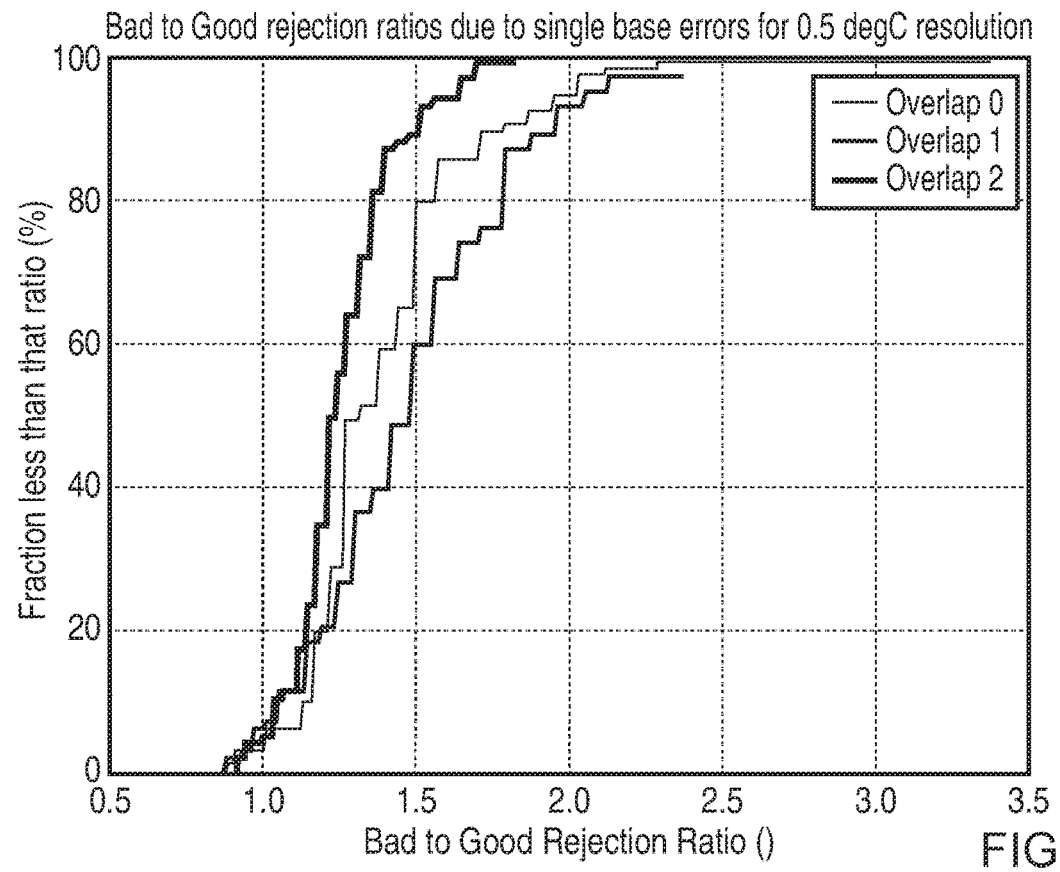
Figure 22:
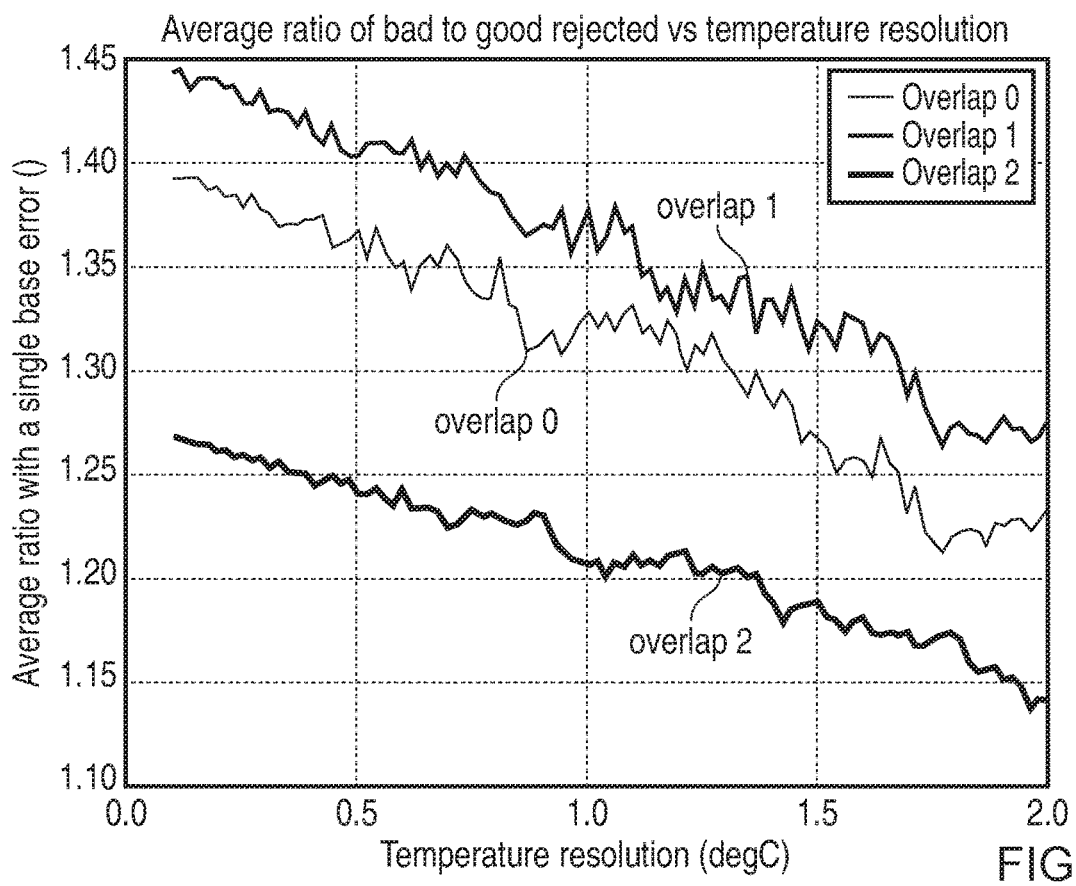
Figure 23:
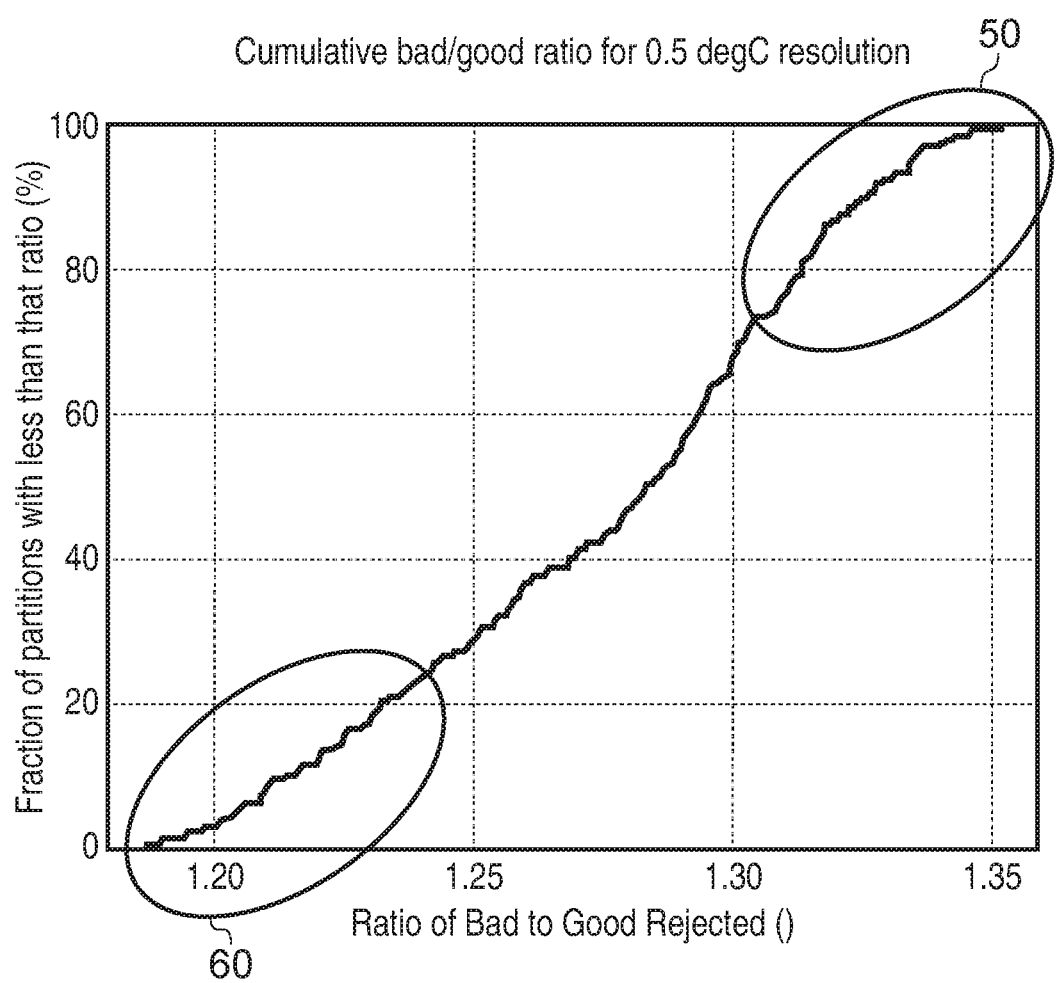

FIGS. 6 to 8 compare pooled, sequential and binary assembly processes and show how in the binary assembly process where both of the pair of earlier hybridisation steps feeding into a given hybridisation step involve error detection, the yield can be improved;

FIG. 9 shows an example of a tree of hybridisation steps using the binary assembly process in which at least one further hybridisation step combines products of a pair of error-detecting hybridisation steps;

FIGS. 10 and 11 illustrate an example of an apparatus on which the binary assembly process can be carried out;

FIG. 12 illustrates a method of performing an error-detecting type of hybridisation step;

FIGS. 13A to 13F schematically illustrate a worked example of performing a tree of hybridisations using the binary assembly process with error detection;

FIGS. 14A and 14B illustrate how switching which strand of the target double-stranded nucleic acid molecule is bound to a surface of a reaction site between successive hybridisation steps prevents erroneous fragments detected at a previous hybridisation step from hybridising with error-free fragments at a next hybridisation step;

FIG. 15 is a graph illustrating how percentage yield of error-free DNA generated with the binary assembly process scales with length, for a number of different error detection rates of the error detection operation;

FIG. 16 is a graph showing the relative improvement in the yield achieved in the binary assembly process compared to the yield achieved with a pooled or sub-pooled approach;

FIG. 17 illustrates an alternative technique for implementing the binary assembly process;

FIG. 18 illustrates an example of hybridisation of four fragments at three overlap regions (complete sequence, SEQ ID NO: 2; s1, SEQ ID NO: 3; a1, SEQ ID NO: 4; s2, SEQ ID NO: 5; a2, SEQ ID NO: 6);

FIG. 19 is a graph illustrating how percentage helicity (percentage of bonds in the DNA molecule remaining intact when heated to a given temperature) scales with temperature for the three overlap regions of FIG. 18;

FIG. 20 is a graph illustrating, for each of the three overlap regions, and considering all possible erroneous double-stranded fragments which comprise a single base error within that overlap region, the percentage of those erroneous double-stranded fragments for which the expected melt temperature difference relative to an error-free double-stranded fragment would be less than a given temperature difference;

FIG. 21 is a graph illustrating cumulative distribution of "bad" to "good" fragment rejection ratios, among all possible erroneous fragments which have at least one base error in an overlap region, when errors are detected with a 0.5° C. temperature margin below the expected melt temperature of the overlap region in "good" fragments, for the three overlap regions;

FIG. 22 is a graph illustrating how the average rejection ratio across all possible erroneous fragments varies with temperature resolution for the three overlap regions; and FIG. 23 is a graph illustrating the cumulative distribution of averaged single-base mismatch concentration ratio across three overlaps over all possible partitions of an example DNA sequence.

In the subsequent examples, for conciseness DNA is used as an example of a double-stranded nucleic acid. It will be appreciated that this technique could also be used to assemble other types of double-stranded nucleic acid, such as RNA or XNA (xeno nucleic acids, a synthetic alternative to the natural nucleic acids DNA and RNA).

The technique described below provides a method for assembling sequences of DNA from many shorter oligonucleotides, which can result in higher yields of error-free sequences of DNA or genes when compared to other assembly techniques. In approaches based on pooling or sub-pooling, occasional errors in the synthesised oligonucleotides accumulate randomly throughout the assembly process and dramatically reduce yield of error-free double-stranded DNA as sequence length increases. The result is that expensive and time-consuming techniques such as cloning and error-correction are required to obtain error-free sequences before final assembly. The method described here avoids this problem, tolerating the finite error rate by detecting and removing erroneous fragments in at least one intermediate point in a staged and controlled hybridisation process. Oligonucleotides with sequence errors are prevented from diluting the pool of error-free double-stranded DNA at a subsequent hybridisation step. Control over the timing at which certain fragments are brought together is provided enabling oligonucleotides and DNA fragments to be combined in specific order, and a method for detecting and removing erroneous sequences during hybridisation. The benefit increases in proportion to sequence length, enabling the de novo synthesis of long DNA fragments in a streamlined and integrated process without the need for external purification techniques.

FIG. 1 schematically illustrates an example of a sequence of DNA, formed of two complementary strands A, B of bases A, G, C, T such that each base A, T, G, C in one strand has a complementary base T, A, C, G in the other strand. One strand A corresponds to the sense (5' to 3' direction) strand and the other strand B corresponds to the antisense (3' to 5' direction) strand. Each strand is partitioned into a number of partially overlapping single-stranded fragments A1-A5 and B1-B5. Excluding the fragments A1, A5, B1, B5 at either end of each strand, the intermediate fragments A2-A4 and B2-B4 each span two different fragments of the other strand (e.g. fragment B3 of strand B spans across part of fragments A2 and A3 of strand A). The region at which a given pair of partially overlapping fragments, one from each strand, overlap is referred to as an overlap region. For example, the overlap region between fragments A3 and B2 in this example corresponds to bases 5'-GCTC-3' in fragment A3 and complementary bases 3'-CGAG-5' in fragment B2.

Synthetic DNA is commonly assembled from many shorter oligonucleotides in a process called pooling, a strategy that requires unique sequences in the overlap regions to ensure correct hybridisation. The top part of FIG. 2 illustrates a pooled assembly approach, where once all the single-stranded fragments A1-A5 and B1-B5 have been formed, they are placed within a common container. By selecting the locations in the respective strands at which the strands A, B are partitioned into the fragments so that each overlap region has a unique sequence compared to other overlap regions, then when the fragments are all placed in the container, each fragment will hybridise with the correct other fragments which have complementary overlap regions, e.g. fragment A3 will hybridise at one end with B3 and at the other end with B2. The relative order in which each overlap region is hybridised is random and uncontrolled—e.g. some instances of A3 will hybridise with B3 before B2, while other instances of A3 will hybridise with B2 before B3.

As the number of possible unique sequences, n, increases exponentially with the overlap length (l), n=4$^l$, the sequences can be practically unique once the overlap exceeds a certain value (20 to 30 base pairs is common—shorter overlaps of 3-5 bases being shown in FIG. 1 for conciseness). However, this situation is complicated by the presence of highly repetitive sequences, which reduce the number of possible combinations drastically, or regions that are GC or AT rich (GC bonds are stronger than AT, so that mismatched GC-rich sequences may be as likely to bond as correctly matched ones). For this reason, it is common practice to stage assembly in sub-pools to reduce the chances of incorrect hybridisation. The lower part of FIG. 2 illustrates how by initially placing different subsets of fragments of the overall target DNA molecule in different containers, so as to prevent the fragments in one subset hybridising with the fragments in the other subset, this can allow longer DNA molecules to be formed even if the overlap region sequences in one part of the DNA molecule are no longer unique when compared to overlap region sequences in another DNA molecule. Once each sub-pool has been hybridised, the resulting partial DNA fragments can then be brought together to hybridise further to form the overall DNA molecule.

Figure 3:
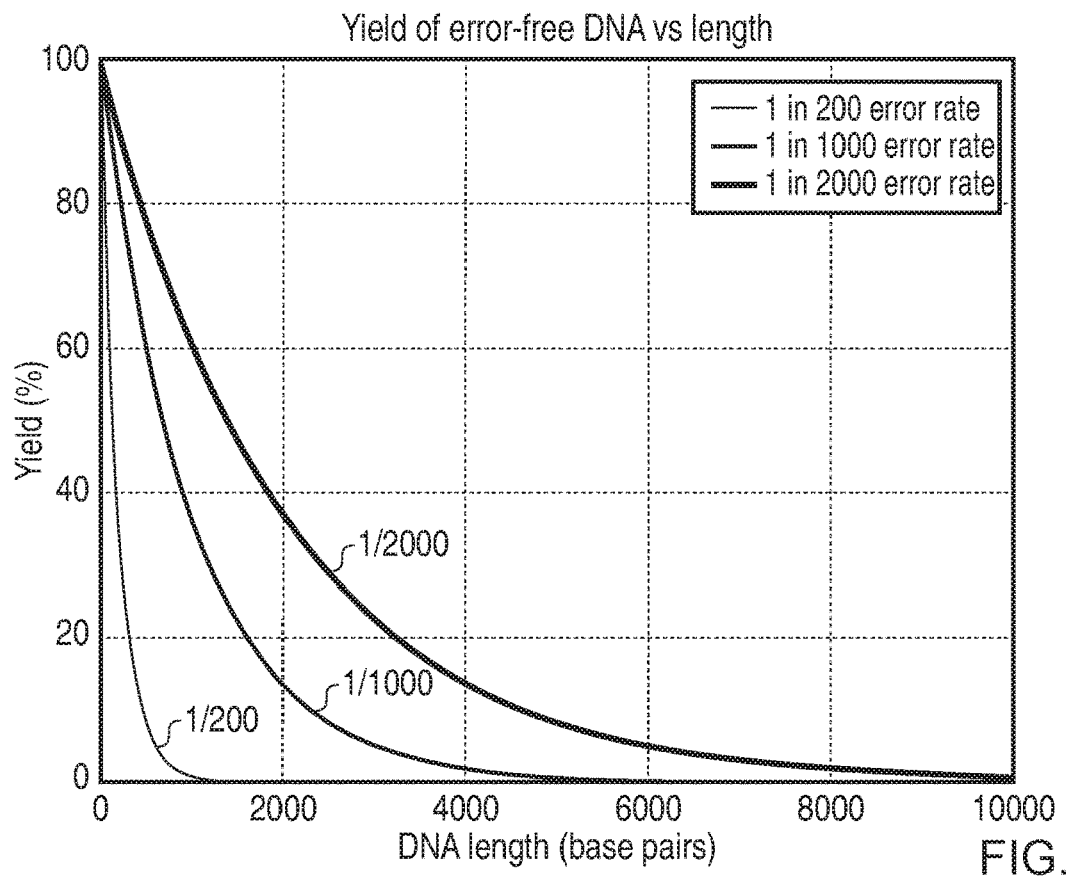
FIG. 3 is a graph illustrating percentage yield of error-free DNA expected for various lengths of DNA sequence made using a pooled or sub-pooled assembly process.

Approaches that are based on pooling or sub-pooling share the disadvantage that it is only possible to detect or correct errors once the entire pool or sub-pool has hybridised. It is possible to apply some error detection techniques (e.g. using enzymes) on the originally formed single-stranded fragments A1-A5, B1-B5 before any of the hybridisations take place, but this can be slow and expensive and may still allow a significant rate of errors to be undetected. Hence, occasional errors in synthesised oligonucleotides (truncations, deletions, insertions or mis-incorporations) randomly accumulate throughout the hybridisation process and dramatically reduce the yield of error-free DNA as the assembled DNA fragment length increases. If the error rate, or independent probability of an error in any base position, is $P_e$ then the yield, Y, of error-free DNA cannot exceed the probability of zero occurrences of an error over n trials, $Y \leq (1-P_e)^n$, which is shown graphically for several different error rates in FIG. 3.

This limitation depends only on the length of DNA that is produced, not on the length of oligonucleotides used to assemble that DNA, or on the number of sub-pooling steps (sub-pooling only reduces the probability of mishybridisations due to an overlap region of one fragment matching against an overlap region of an incorrect fragment which the first fragment is not supposed to be hybridised with, but does not reduce the effect of incorporation errors in the initial batch of single-strand fragments on yield). It is for this reason that it is not currently practical to synthesise fragments greater than a few thousand bases directly using phosphoramidite chemistry, with an error rate of around 1 in 200. It should also be apparent from FIG. 3 that very significant reductions in the incorporation error rate in oligonucleotide synthesis would be necessary to achieve modest increases in DNA length. Instead, error-free fragments are selected from sub-pools by cloning and sequencing before subsequent assembly to form larger fragments, a process that is both expensive and time-consuming.

Figure 4:
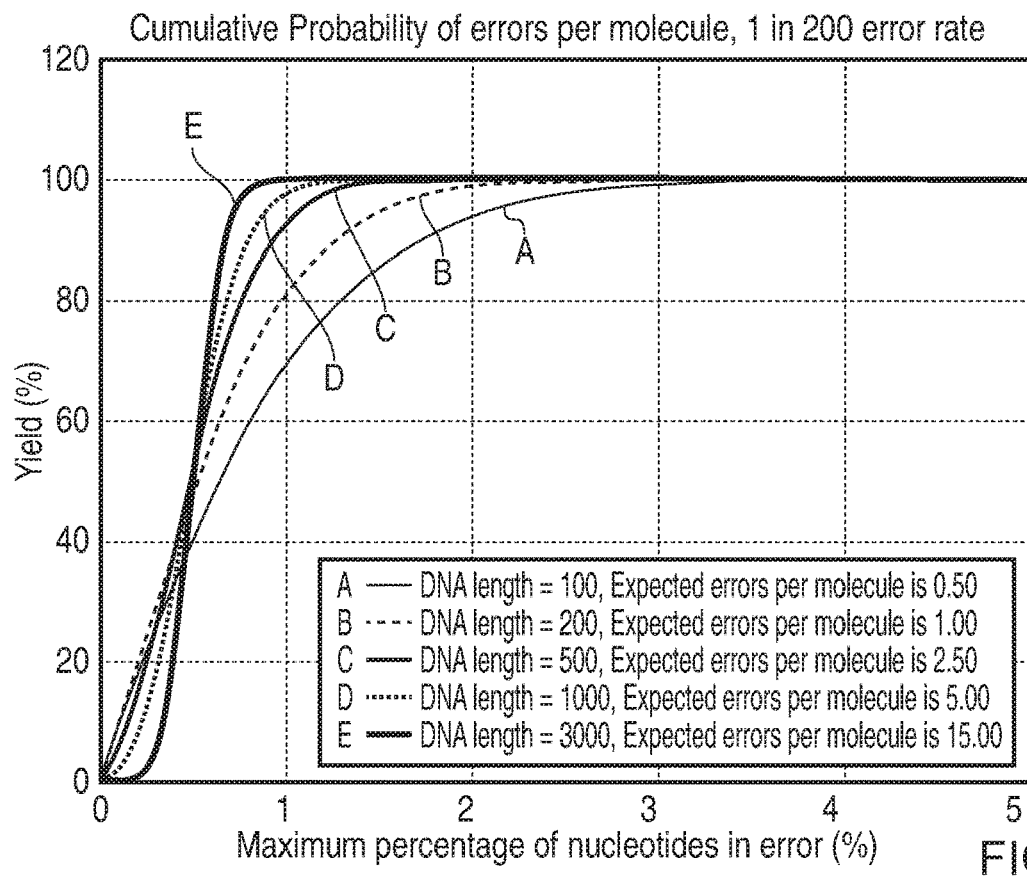
FIG. 4 is a graph illustrating cumulative probability of errors per molecule for different lengths of DNA molecule.
Figure 5:
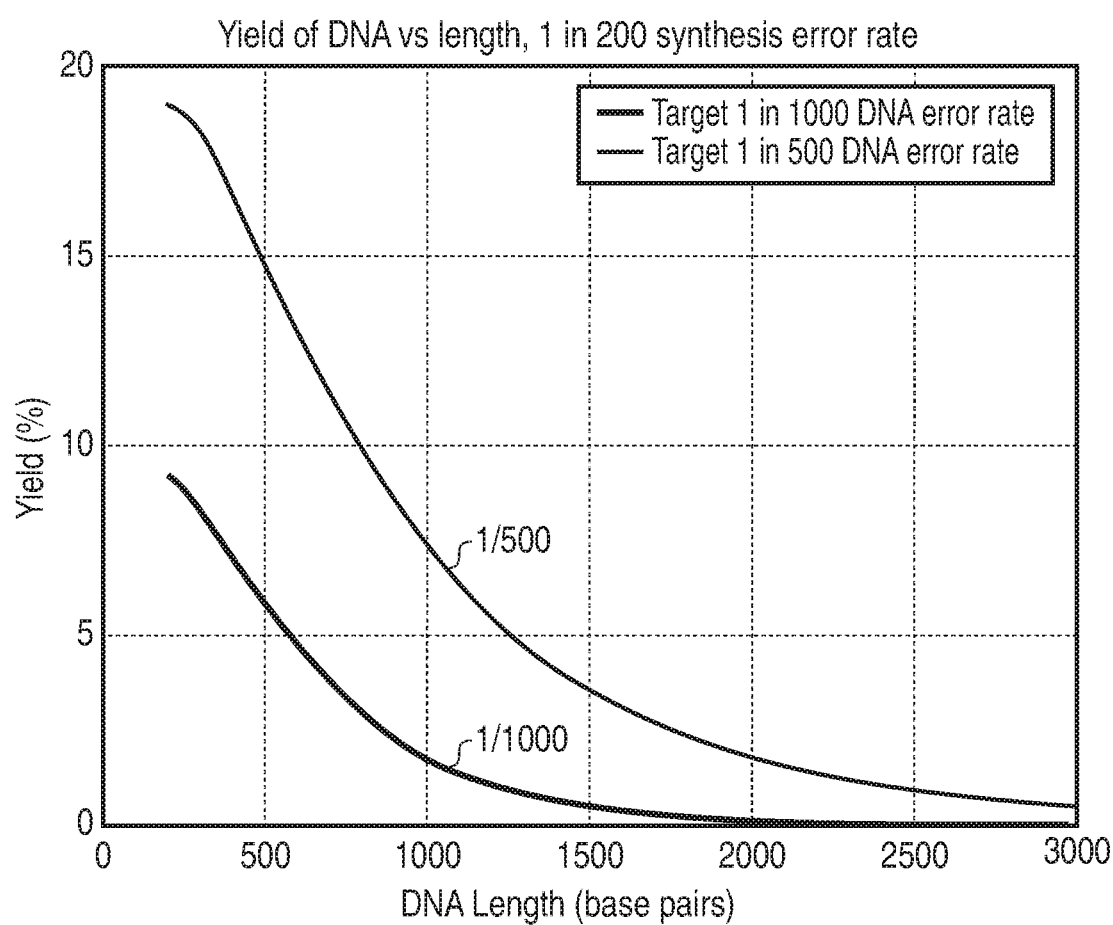
FIG. 5 is a graph illustrating how percentage yield of DNA made using the pooled or sub-pooled assembly process scales with DNA length, when a certain maximum error rate can be tolerated.

However, it is not always necessary to have completely error-free DNA, with certain applications able to tolerate some given error rate. The probability density of the number of errors, m, in a population of assembled DNA of length n is binomial and given by:

$$P(m, n) = \frac{n!}{m!(n-m)!}(1-P_e)^{(n-m)}(P_e)^m$$

which has an expected value of errors per DNA molecule of $E(n)=n(1-P_e)$. The cumulative distribution $$C(m, n) = \sum_{i=0}^{m} P(i, n)$$

can be used to calculate the probability that the number of errors will be below any number, m. For a large population of DNA molecules, this is the fraction of molecules with m or less errors, or the yield for a given maximum number of errors. FIG. 4 illustrates the cumulative probability of errors per molecule, for different DNA lengths, when assuming that the incorporation errors occur with a 1 in 200 error rate. As can be seen from FIG. 4, as the length of DNA increases relative to the error rate, most DNA molecules will have the expected number of errors, and very few will have less errors than expected (since the gradient of the cumulative probability line is much steeper for DNA length 3000 compared to DNA length 100, this indicates that there is less variation in the number of errors expected from molecule to molecule—most molecules with length 3000 have around 0.05% of nucleotides in error, i.e. 1 in 200). Hence, similar graphs to the error-free yield limitation shown in FIG. 3 can therefore be constructed for arbitrary desired target error rates (fraction of nucleotides in error per molecule), but these will always show an exponential decrease in yield with DNA length if the desired accuracy exceeds that suggested by the fundamental error rate, $(1-P_e)$. An example is shown in the graph of FIG. 5. Assuming that the rate with which incorporation errors occur in the initial batch of fragments is 1 in 200, FIG. 5 illustrates how the percentage of DNA molecules made using the pooled or sub-pooled technique that has less than the target DNA error rate (fraction of nucleotides in error in one molecule) scales with DNA length, for two example target DNA rates of 1 in 1000 and 1 in 500. It can be seen that even when as high a fraction as 1 in 500 nucleotides per DNA molecule are permitted to be in error, as length increases the yield of DNA meeting the target DNA error rate is still low and drops off rapidly with length.

FIGS. 6 to 8 show a number of alternative assembly approaches, to illustrate the differences in error-free yield achieved. FIG. 6 shows the simple pooled or sub-pooled approach discussed above. FIG. 7 shows a sequential assembly approach. FIG. 8 shows a binary assembly approach. These diagrams, for ease of understanding, show the hybridisation of only four fragments of DNA labelled A1, B1, A2, B2, where the overlap regions are such that the fragments would hybridise to form a sequence A1-B1-A2-B2 where the overlaps are between A1/B1, B1/A2 and A2/B2 respectively. To make comparisons of error-free yield more apparent, the incorporation (synthesis) error rate in the initial single-stranded fragments A1-B2 is assumed to be an artificially high 50%, i.e. 50% of each batch of fragments A1, B1, A2 and B2 are erroneous as they contain at least one incorrect base (whether due to mis-incorporation, truncation, deletion or insertion). Clearly, lower incorporation error rates are likely in practice, but even if the actual incorporation error rate is lower, the binary assembly approach of FIG. 8 would still result in higher yield compared to the alternative approaches. In each box shown in FIGS. 6-8, the hatched area shows the percentage yield of "good" fragments remaining at that stage of hybridisation, which represents the fraction of "good" error-free fragments relative to the number of instances of each initial fragment A1, B1, A2, B2. That is, if N instances of each initial fragment are provided, and the number of instances of "good" hybridised fragments at a later stage of hybridisation is G, the yield corresponds to G/N.

FIG. 6 shows an example of applying the pooled approach, where all the fragments are simply placed in a common container and allowed to hybridise at the matching overlap regions. As each of the four initial batches of fragments has 50% erroneous fragments, and the sequence of hybridisation is uncontrolled, the yield of error-free instances of the assembled sequence A1-B1-A2-B2 remaining after the hybridisation is complete is 0.5*0.5*0.5*0.5=0.0625, i.e. rounded to the nearest integer a 6% error free yield. Even if sub-pooling is used, this would still result in the two separate sub-pools A1/B1 and A2/B2 producing a 25% yield (0.5*0.5), and then the hybridisation between the two sub-pools would result in a quarter of the "good" fragments in one sub-pool being paired with "good" fragments from the other sub-pool, i.e. the error-free yield would still be 0.25*0.25=0.0625, i.e. 6% again.

FIG. 7 shows, for comparison, an example of a sequential assembly process, where first a pair of single-stranded fragments A1, B1 are hybridised, erroneous hybridised fragments are detected and discarded after that hybridisation, before then hybridising the remaining error-free fragments A1-B1 with the next single-stranded fragment A2. Again, erroneous fragments are detected and discarded, before hybridising the remaining error-free fragments A1-B1-A2 with the final single-stranded fragment B2. One might think that eliminating the erroneous fragments after each hybridisation would help to improve yield. However, as the single-stranded fragment added in each successive sequential hybridisation still contains 50% erroneous fragments, half the error-free fragments resulting from the previous hybridisation step are paired with erroneous fragments at the next hybridisation step, and the result is that the yield of error-free fragments, relative to the amount of initial material, is still the same as in FIG. 6. The elimination of erroneous fragments at each hybridisation step only achieves a reduction in the quantity of erroneous fragments which are still present at the final hybridisation step (in FIG. 7 the 6% yield relative to the amount of initial material now represents 50% of the remaining fragments, rather than 6% of the remaining fragments as in FIG. 6). Nevertheless, the amount of useful material made for a given quantity of input material is not any greater than in FIG. 6.

FIG. 8 shows a binary assembly process with error detection, in which a further hybridisation step $H_F$ hybridises the direct products of a pair of earlier hybridisation steps $H_E$, both of which are error-detecting hybridisation steps which include a step of detecting erroneous fragments formed in the hybridisation step and discarding part of each detected erroneous fragment so that it is excluded from the subsequent further hybridisation step $H_F$. Hence, while each of the earlier hybridisation steps $H_E$ still produce a useful yield of 25% (0.5*0.5) relative to the amount of initial material provided, the 75% erroneous fragments are detected and discarded, leaving a purified population of "good" fragments which are then hybridised together in the further hybridisation step $H_F$. As there are no erroneous fragments remaining, the further hybridisation step $H_F$ does not reduce the yield any further, as all "good" fragments are paired with other "good" fragments. Therefore, the resulting yield at the end of the further hybridisation step $H_F$ is still 25%, significantly improved relative to 6% in FIG. 6 or 7. Of course, in practice the synthesis error rate is unlikely to be as high as 50%, the error detection operation performed after the earlier hybridisation steps $H_E$ may not be 100% accurate at detecting erroneous fragments, and there may be other loss mechanisms which lead to loss of "good" fragments, but as explained below, even if the error detection rate is lower and there is some additional loss, as the total length of DNA synthesised becomes longer and longer, the relative improvement of the approach shown in FIG. 8 relative to FIG. 6 or 7 becomes greater and greater.

FIGS. 6 to 8 show an example with four fragments being hybridised to form the target DNA molecule, but as shown in FIG. 9 further hybridisations may be performed in sequence to form a tree of hybridisations. The initial fragments provided as source material for the sequence of hybridisations could be double-stranded fragments already partially hybridised from single-stranded fragments, or more commonly may be single-stranded fragments such that the initial hybridisation steps are the first time that partially-overlapping double-stranded fragments of DNA are produced. In this example, the initial fragments are single stranded fragments A1, B4, A2 etc. (as shown in FIG. 1). The tree of hybridisations includes a number of initial hybridisation steps $H_1$-$H_4$ hybridising respective pairs of initial fragments provided as source material for the hybridisation process, and a number of further hybridisation steps $H_5$, $H_6$, $H_7$ which hybridise pairs of fragments generated in earlier hybridisation steps (the earlier hybridisation steps could be either an initial hybridisation step or a later hybridisation step). If the number of initial fragment is an exact power of 2 (e.g. if only fragments A1-A4 and B1-B4 were provided), the tree of hybridisations forms a full binary tree as shown in steps $H_1$ to $H_7$ in FIG. 9. If the number of initial fragments is not a power of 2 (e.g. if there is an additional fragment A5 as shown in the dotted lines of FIG. 9), then there may also need to be some additional hybridisation steps which hybridise a result of an earlier hybridisation step with an initial fragment which has not yet undergone hybridisation. Similarly the hybridisation of B5 with A1 may require an additional hybridisation step not shown in FIG. 9 for conciseness.

Each hybridisation step H corresponds to a particular overlap region of the target DNA sequence, and hybridises one or more respective pairs of fragments at that particular overlap region. E.g. initial hybridisation step $H_2$ in this example corresponds to the overlap between single-stranded fragments A2 and B3, and further hybridisation step $H_7$ in this example corresponds to the overlap between single-stranded fragments B3-A3, and hybridises one or more respective pairs of fragments A1-B4-A2-B3 resulting from earlier hybridisation $H_5$ and A3-B2-A4-B1 resulting from earlier hybridisation $H_6$. Each hybridisation step may be repeated multiple times on respective batches of each of the corresponding pair of fragments, to form a corresponding batch of the hybridised fragments.

Any of the further hybridisation steps $H_5$-$H_7$ may correspond to the further hybridisation step $H_F$ shown in FIG. 8, so that both of the earlier hybridisation steps $H_E$ which feed into that hybridisation step include the error detecting operation. In the example of FIG. 9, the hybridisation steps $H_1$ and $H_2$ are error detecting operations, so that the yield of the double-stranded fragment B4-A2 produced at the next hybridisation step $H_5$ can be improved for the reasons explained with reference to FIG. 8. Similarly, if $H_3$ and $H_4$ are the error-detecting type of hybridisation, then the yield produced at the subsequent step $H_6$ can be improved (having a knock on effect on yield at subsequent steps), and if $H_5$ and $H_6$ are the error-detecting type of hybridisation step, then the yield produced at $H_7$ can be improved.

Yield can be highest if every hybridisation step is of the error-detecting type. This is because the error detection mechanism described below may only be able to detect errors in the overlap region being hybridised at the corresponding hybridisation step, so that error detection operations are needed at each hybridisation in order to extend the region at which errors can be detected to the entire sequence of the target DNA molecule being assembled. Nevertheless, it is not essential for every hybridisation to be of the error-detecting type—some error detecting operations may be omitted to save time and improve processing speed, as in this case multiple levels of the hybridisation tree can be combined at a single site.

It will be appreciated that FIG. 9 only shows the relative sequencing of the hybridisations, but does not show the absolute timings. That is, the sequencing is such that hybridisations $H_1$ and $H_2$ need to be completed before further hybridisations $H_5$ or $H_7$ can be performed, as both $H_5$ or $H_7$ are dependent on the results of $H_1$ and $H_2$. However, as $H_3$, $H_4$ and $H_6$ are independent of $H_5$, it does not matter whether $H_3$, $H_4$ and $H_6$ are performed before or after $H_5$. While the process can be fastest if all of the hybridisation steps at a given level of the tree are performed in parallel, this is not essential and there is flexibility to alter the relative timing between independent hybridisations.

The error detecting operation performed for each error-detecting type of hybridisation step can be performed without exporting the results of the hybridisation step to a host for cloning and sequencing. Instead, the error detecting operation is performed on the hybridised fragments formed in the error-detecting type of hybridisation step, and the remaining fragments not discarded in the error detection operation are forwarded directly to the next hybridisation step, so that the next hybridisation step acts on the direct product (same molecules) produced by the previous hybridisation step, not on cloned copies of the molecules produced in the previous hybridisation step. Hence, the process can be much faster than processes involving cloning. Note that operations (such as ligation) may be performed on the molecules produced in the previous hybridisation step before performing the next hybridisation step, where such operations merely modify the existing molecules rather than generating entirely new molecules—the results of such intervening operations are still considered to be the direct product of the previous hybridisation step since the further hybridisation is performed on the physically same molecules that were generated in the previous hybridisation step.

FIGS. 10 and 11 illustrate a device 2 on which the binary assembly process discussed above can be performed. For conciseness, any mechanisms for creating electric or magnetic traps are not shown, but could still be provided. As shown in FIG. 10, a fluid flow element (e.g. a pump) is provided to control the flow of fluid through a fluid flow path 4 across the top of the device 2. A number of reaction sites (active thermal sites) 6 are provided at various locations across the plane of the temperature control device 2. The top of each reaction site 6 may include a reaction surface (e.g. a gold cap) on which the growth of single-stranded nucleic acid fragments or hybridisation steps can take place. Each reaction site 6 corresponds to part of a level surface, so that there is no physical barrier between adjacent reaction sites 6. Each reaction site 6 has a heating element 7 provided below the reaction site surface to apply heat to the corresponding part of the fluid flowing over that site, to control the temperature of the fluid for performing the error detection. As shown in FIG. 11, the reaction sites 6 are arranged in a two-dimensional matrix (grid), arranged in two or more rows (lanes) 9 where the lane/row direction is parallel to the direction that fluid flows through the fluid flow path 4. The regions lying between the active thermal sites 6 form one or more passive thermal regions 8 which do not comprise any heating element, but provide passive cooling by conducting heat away from the fluid towards the substrate 10 of the device 2. The length x of each active thermal site 6 in the row direction is longer than the length y of each passive thermal region 8 lying between a pair of adjacent active thermal sites 6 in the same row. The thermal resistance of the material provided below each active thermal site 6 in a direction perpendicular to the substrate may be greater than the thermal resistance in the direction perpendicular to the substrate of the material provided below each passive thermal region 8. As shown in FIG. 10, a cooling mechanism 12 may be provided to cool the substrate 10 to act as a heat sink.

Alternatively, rather than using the active and passive regions 6, 8 to control temperature through active heating at the active sites and passive cooling to the heat sink 10 at the cooling sites, an array of reaction sites may have their temperature controlled using a single thermo-electric cooling element which uses the Peltier effect to transfer heat to or from the reaction site depending on a control current supplied to the thermo-electric cooling element (e.g. the control system of WO 2017/006119 A2 can be used).

In use, the oligonucleotides or other initial fragments to be hybridised together may be grown on the respective reaction sites 6 of a given lane of the device 2, or may be anchored to the reaction sites 6 after having been formed elsewhere. Each reaction site 6 anchors many oligonucleotides of the same sequence, with different sequences on different sites 6. Groups of oligonucleotides can be released from the reaction sites independently and transported to hybridise with their neighbours in pairs. Errors in the oligonucleotides can be detected by testing the bond strength of these hybridised overlap regions, with subsequent removal of erroneous oligonucleotides. This process is then repeated to join pairs of the resulting fragments, extending the length of the fragments at each pair-wise hybridisation step. The direction of the complementary overlap sequence is reversed at each hybridisation so that every nucleotide is tested as part of a single or double-stranded fragment released from the substrate and erroneous fragments are able to be removed without hybridising to "good" fragments at a subsequent step. Thermal control can be used as the mechanism for testing the strength of the hybridised bonds, with erroneous fragments being removed by the flow.

The result of removing erroneous fragments after each pair-wise hybridisation is that these errors are prevented from diluting the pool of error-free fragments, drastically improving the yield of error-free DNA as length increases. With this process, the yield of error-free DNA no longer drops so aggressively with length, but instead follows a more gradual decrease that depends on the efficacy of error detection and details such as transport loss and hybridisation efficiency. Very significant improvements in yield of error-free DNA can therefore be obtained for long sequences, with an improvement over any existing technique that increases with DNA length.

FIG. 12 shows a flow diagram illustrating a method of performing an error-detecting type of hybridisation step (which could be any of the hybridisation steps shown in FIG. 9 for example). At step 20, a number of hybridisations are performed on the corresponding pair of fragments which overlap at the relevant overlap region corresponding to that particular hybridisation step, to form multiple hybridised fragments bonded at that overlap region. Some of the hybridised fragments may be erroneous due to the presence of an incorporation error in one of the initial fragments at a location corresponding to the overlap region hybridised in that hybridisation step.

Steps 22 and 24 represent an error detection operation performed in the error-detecting type of hybridisation step performed at a given reaction site. At step 22, the temperature of the given reaction site is controlled to be set to a temperature which is a margin below the expected melting temperature of the overlap region formed in the corresponding hybridisation step for an error-free hybridised fragment which does not comprise a base error within that overlap region (note that the error-free hybridised fragment could still have base errors in other parts of the sequence outside the overlap region, which are not tested in this particular error detection step). The particular temperature to be used for the given reaction site can be determined for each hybridisation step using computer simulation of the expected melt temperature for different sequences of bases in the overlap regions and the ratio of "bad" fragments to "good" fragments that would be rejected by setting the temperature to a particular level, as will be discussed in more detail below. By setting the temperature to a margin below the expected melt temperature, it is more likely that the erroneous fragments, which have at least one base error in the overlap region, will dissociate, than the "good" fragments which have perfectly matching sequences of bases in the overlap region. At step 24, fluid is washed over the hybridised fragments at the reaction site to wash away the part of the fragment on the "non-bound" or "loose" strand of the fragment (the strand which was not directly fixed to the surface of the reaction site). As erroneous fragments are more likely to have their bonds weakened by the temperature adjusting step than the "good" fragments, more of the erroneous fragments are discarded in the flowing fluid while remaining fragments remain fixed to the surface. The bound half of each erroneous fragment remains fixed to the surface, but the alternation of which strand is bound to the surface between successive hybridisation steps prevents these orphaned fragments hybridising at subsequent steps when the bound fragments are subsequently released at step 28.

At step 26 a ligation step is performed, in which the remaining fragments after the non-bound parts of erroneous fragments are washed away are exposed to a ligation enzyme which joins the sugar-phosphate backbone between adjacent single-stranded fragments of the same strand. The ligation step may be omitted if the hybridisation step is an initial hybridisation step performed on two single-stranded fragments. E.g. in the hybridisation step H5 shown in FIG. 9, following hybridisation of the overlap region B4-A2 at step 20 and detecting/discarding erroneous fragments at steps 22, 24, the ligation step 26 may ligate the sugar-phosphate backbone between fragments A1 and A2 of strand A and between fragments B3 and B4 of strand B, to prevent the hybridised fragment dissociating even if subsequently heated above or to the melt temperature of the overlap region between B4 and A2.

At step 28, remaining fragments are released from the given reaction site. The release mechanism could be provided by attaching the fragments to the reaction site via a cleavable linker substance, which can be cleaved by exposing the linker substance to another cleaving substance, or by heating to a given temperature. Alternatively, the release could be activated by an enzyme, e.g. the examples given above. Examples of cleavable linker substances include a chemical composition having a succinate moiety bound to a nucleotide moiety such that cleavage produces a 3' hydroxy nucleotide. More particularly, the cleavable linker may be one of 5'-dimethoxytrityl-thymidine-3'-succinate, 4-N-benzoyl-5'-dimethoxytrityl-deoxycytidine-3'-succinate, 1-N-benzoyl-5'-dimethoxytrityl-deoxyadenosine-3'-succinate, 2-N-isobutyryl-5'-dimethoxytrityl-deoxyguanosone-3'-succinate, or combinations thereof. In some embodiments, in addition to the flow channels provided for the main transport fluid itself, a network of supply channels could be provided with control valves to allow selective supply of reagents or enzymes to a particular reaction site, to allow targeted release of fragments from a particular site. Alternatively, a temperature-deactivated linker may be used so that release of fragments from a given reaction site is triggered by adjusting the temperature of the corresponding site to a release temperature. For example, enzymes which become active at a given temperature may be used and only the required sites at which fragments are to be released may be heated to the activation temperature of the enzymes. Regardless of the particular release mechanism used, for all but the final hybridisation step which forms the target nucleic acid, the fragments released from the given reaction site are then transported in the flowing fluid provided by the fluid flow path 4 to a next reaction site at which a subsequent hybridisation is to take place. The use of electric or magnetic traps can be used to keep the complementary fragments close to each other (even if they melted during the detachment release due to the increase in temperature to active the cleavage mechanism) and help the transport from one reaction site to another. That is, the traps at the given reaction site can be activated before raising the temperature to the temperature needed to detach the fragments from the given reaction site, then lowering the temperature again once the fragments have been released while the traps still remain active, before then deactivating the traps once the temperature has been lowered. This means that even if the release temperature of the attachment mechanism is higher than the melting temperature of some of the fragments, the fragments are kept together by the traps until the temperature has been lowered again, and can then re-anneal before the traps are released to transport the fragments to the next site. Any known method for manipulating or trapping nucleic acid fragments using magnetic or electric fields may be used (e.g. using electrostatic, electrophoretic, or dielectrophoretic traps).

FIGS. 13A to 13F show the binary assembly process in action for a simplified example of hybridising 8 single-stranded fragments A1-A4 and B1-B4 together, which are intended to hybridise together in the pattern shown in FIG. 1 (for conciseness, the hybridisation steps with A5 and B5, as well as any use of traps, are not shown). It will be appreciated that the steps shown in FIGS. 13A to 13F may form part of a larger tree of hybridisations to form a longer DNA molecule. For ease of understanding, each initial single-stranded fragment A1-A4 and B1-B4 is shown as having the same length in FIGS. 13A to 13F (with the arrow pointing in the 5'-to-3' direction), but in practice as shown in FIG. 1 different fragments may have different numbers of bases. Each initial batch of a given type of initial fragment comprises 3 instances of the fragment in this example—clearly in practice many more instances of each fragment would be provided on each site. The positions of erroneous nucleotides are marked with a cross in FIG. 13A. Of course, insertion, deletion or truncation errors could in practice result in multiple erroneous nucleotides within the same fragment, but for conciseness each error for this example is assumed to be a mis-incorporation error where only a single nucleotide has been erroneously replaced with an alternative nucleotide.

Figure 13A:
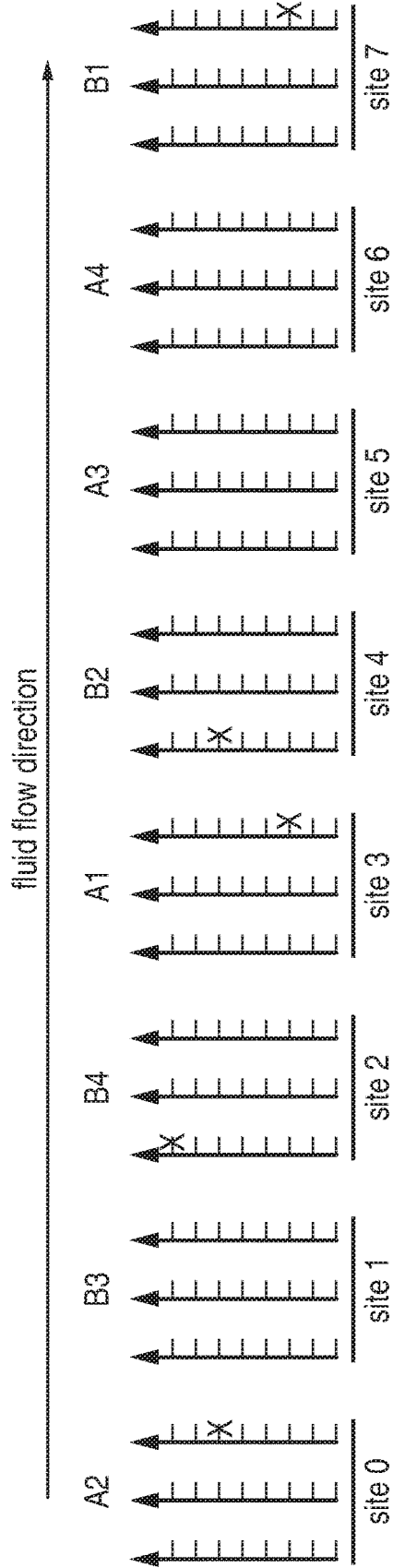

As shown in FIG. 13A, the initial fragments are either synthesised in situ on the corresponding reaction sites, or applied to the reaction sites after synthesis elsewhere, and are bound to each site via a cleavable linker mechanism. The initial arrangement of the fragments is selected so that the process is started with alternate sense (A) and antisense (B) fragments on different reaction sites. The pattern begins as sense (A) on the first site and antisense (B) on the second site. For every doubling of the number of sites, the new sites added on the right are the complement (i.e. A→B, B→A) of the existing sites on the left. Hence, the first few patterns are: AB, ABBA, ABBABAAB, ABBABAABBAABABBA, ABBABAABBAABABBABAABABBAABBABAAB, etc. Note that the sense and antisense could be swapped in this pattern. This pattern follows at least a portion of the Thue-Morse sequence. In the Thue-Morse sequence, the $n^{th}$ element $t_n$ of the sequence is 1 if the number of 1s in a binary representation of n is odd, and is 0 if the number of 1s in a binary representation of n is even. Hence, the first 16 elements for n=0 to 15 would be 0110100110010110. The 1s and 0s of the Thue-Morse sequence could be mapped to A and B (sense and antisense) respectively, or vice versa, so 0 could map to one of A and B and 1 to the opposite one of A and B. If the number of initial fragments is not an exact power of 2, the Thue-Morse sequence for the next-highest power of 2 can be truncated to the appropriate length (either by removing the initial portion of the sequence or by removing the final portion of the sequence). For the particular example of FIG. 13A, there are 8 sites, and so the pattern ABBABAAB is used, so that sites 0 to 7 comprise fragments A2, B3, B4, A1, B2, A3, A4, B1 respectively (of course BAABABBA could also have been used—e.g. the order A2 . . . B1 could have been reversed to give B1 . . . A2). In summary, a series of reaction sites may be allocated with sense fragments (bound to the reaction site via the sense strand) and antisense fragments (bound to the reaction site via the antisense strand) such that the sequence of indications of whether a given reaction site is allocated with sense fragments or antisense fragments corresponds to a portion of the Thue-Morse sequence.

In implementations in which the fragments are grown in situ on the corresponding reaction sites, regardless of whether the fragments provided at a given site correspond to the sense (A) or antisense (B) fragments, the fragments are all grown in the same direction. In the example of FIG. 13A the fragments are grown in the 5' to 3' direction (as represented by the arrows pointing upwards), with the 5' end nearest the surface. In other examples the fragments could be grown in the 3' to 5' direction, with the 3' end nearest the surface. Which direction is used depends on whether phosphoramidite chemistry or enzymatic means are used to grow the fragments. Whichever direction the fragments are grown in, the order of the bases in each fragment is chosen to be consistent with the direction in which the corresponding fragment will appear when assembled into the final target nucleic acid molecule.

Note that the example shown in FIGS. 13A to 13F essentially corresponds to the example of FIG. 9, but ignoring the dotted lines as fragment A5 is not provided. Hence, the labels $H_1$ to $H_7$ shown in FIGS. 13B, 13D and 13F refer to the corresponding hybridisation steps of FIG. 9. In this example, it is assumed that each of the hybridisation steps is an error-detecting type of hybridisation step.

Figure 13B:
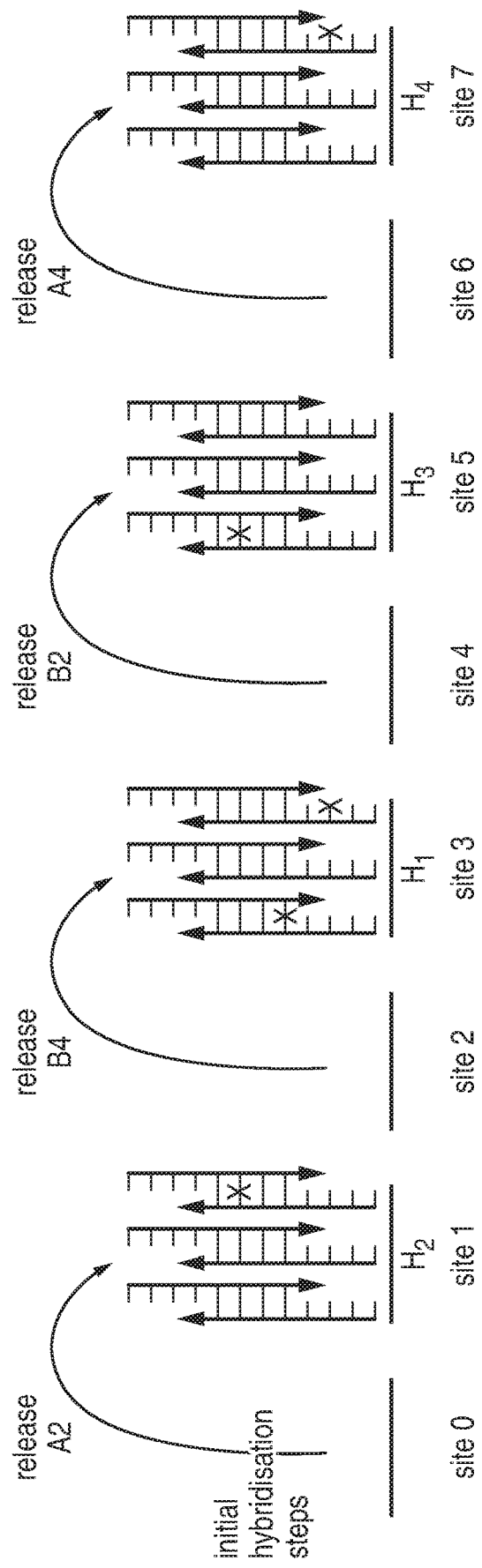

As shown in FIG. 13B, to perform the initial hybridisation steps $H_1$-$H_4$, fragments A2, B4, B2, A4 are released from sites 0, 2, 4 and 6 respectively, e.g. by heating to the release temperature of the linker mechanism or by routing a cleaving enzyme or chemical to the required sites (e.g. using the supply channels discussed above). The fragments at sites 1, 3, 5 and 7 remain bound to the reaction sites. The flowing fluid transports the released fragments from the even-numbered sites to the following odd-numbered site, where the complementary sequences of bases in the overlap regions result in hybridisation at the corresponding overlap regions. If necessary, a barrier mechanism controlled by electric or magnetic fields or using selectively introduced physical barriers can be used to block progress of the released fragments beyond the target reaction site, to stop released fragments passing beyond the next reaction site before they can hybridise. The hybridisation steps $H_2$, $H_1$, $H_3$ and $H_4$ are performed at sites 1, 3, 5 and 7 respectively, to form corresponding double-stranded fragments which still have sticky ends where an overlap region on one strand of the fragment extends beyond the end of the other strand.

FIG. 13C illustrates the error detection step performed for the initial hybridisation steps $H_1$-$H_4$. The temperature at sites 1, 3, 5, 7 is set to a margin (Δ) below an expected melting temperature $T_m$ of the overlap region hybridised at that site. For example, for site 1 the relevant overlap region is between fragments B3 and A2, so the temperature is set to $T_m(B3A2)-\Delta$. In some embodiments, not only the melt temperature, but also the margin $\Delta$ may be selected bespoke for each site, to maximise the fraction of "bad" fragments which are rejected by the error detection relative to "good" fragments. By heating to just below the expected melt temperature of the overlap region in "good" fragments, the erroneous fragments which have an erroneous base in the overlap region are more likely to be separated than the "good" fragments for which the bases perfectly match within the overlap region. The flowing fluid washes away the separated loose parts of erroneous fragments. For example, at site 1 one of the loose A2 fragments had an error and so it separates from the bound fragment B3 at that reaction site and is washed away, leaving B3 as an orphan fragment which has no partner but is still bound to the reaction site. On other occasions, the error could have been on the bound fragment, so that the "good" loose fragment may be discarded even though it does not contain an error (nevertheless discarding the "good" loose fragment is desirable to prevent the erroneous fragment being hybridised with other fragments at a subsequent hybridisation step). Note that among the remaining hybridised fragments where there were no errors in the overlap region hybridised in the current hybridisation steps, there could still be errors in other parts of the fragment outside the overlap region (e.g. see one of the fragments at site 3 and one of the fragments at site 7—these errors can be detected in a later hybridisation step). The ligation step described above is not needed for the initial hybridisation steps shown in FIGS. 13B and 13C, as the hybridisation was performed on pairs of single-stranded fragments.

As shown in FIG. 13D, the fragments at sites 1 and 5 are released and transported in the flowing fluid to the next reaction sites (3 and 7 in this example). The hybridisations performed at sites 3 and 7 correspond to hybridisation steps $H_5$ and $H_6$ of FIG. 9 respectively. The "good" fragments released from sites 1 and 5 are able to hybridise with fragments provided at sites 3 and 7, as they have matching overlap regions (for example, for site 3 corresponding to hybridisation step $H_5$, the overlap is between B4 and A2). However, any orphaned fragments which were detected as erroneous in the previous error detection step, while being transported along with the "good" fragments, will not find a partner at the next site as they do not have the overlap region which can hybridise with the exposed overlap region at the next site. For example, the fragment B3 which was orphaned at site 1 cannot hybridise with the A1-B4 fragments at site 3, because the washed away fragment A2 would have been needed to bridge between B3 and B4 (see FIG. 1). Therefore, the orphaned fragments cannot hybridise. As shown at sites 3 and 7, some "good" fragments at these sites may themselves become orphaned because there are not enough "good" partners with which they can hybridise, rather than because they themselves include an error.

As shown in FIG. 13E, another error detection step is performed as part of the hybridisation steps $H_5$ and $H_6$, in which the sites 3 and 7 are heated to a margin below the expected melt temperature for the corresponding overlap region in "good" fragments. In this particular example, the random locations of the erroneous bases were such that the overlap regions bonded in these hybridisation steps did not contain any errors, so no fragments are discarded, but on other occasions some errors could be detected at this stage. Ligation is performed after the error detection to connect the backbones of the fragments joined in the corresponding hybridisation step, at the locations indicated with circles in FIG. 13E. Effectively, the ligated backbone means that the resulting fragments following FIG. 13E are double-stranded fragments of a longer length than the shorter fragments which were hybridised at step FIG. 13D.

Figure 13F:
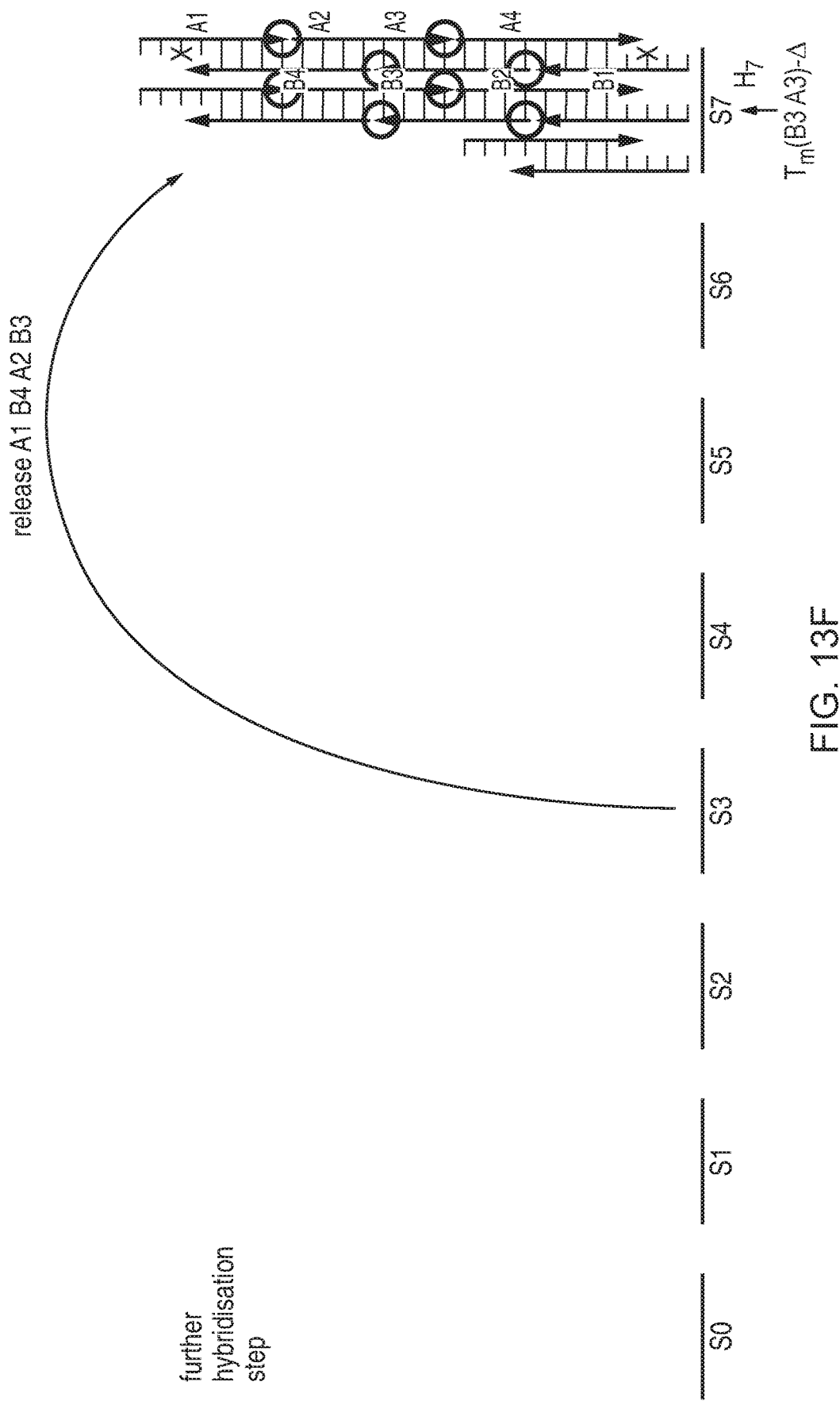

As shown in FIG. 13F, the fragments from site 3 are then released, to hybridise with the fragments at site 7 in hybridisation step $H_7$. Following this hybridisation step, the temperature of site 7 is heated to $T_m(B3A3)-\Delta$ to perform another error detection operation similar to the previous ones, to detect errors in the overlap region A3-B3 hybridised in hybridisation step $H_7$. Note that as the backbone of the nucleic acid at the locations marked with the circles in FIG. 13F were previously ligated, compared to the temperature $T_m(B3A3)-\Delta$ for weakening the bond at the overlap region between A3 and B3 in erroneous fragments, a much higher temperature would be required to dissociate the respective strands along the portion of the nucleic acid with a continuous ligated backbone (i.e. it is relatively difficult to separate A1-A2 from B4-B3 and relatively difficult to separate B1-B2 from A3-A4, compared to separating A1-B4-A2-B3 from A3-B2-A4-B1), so that the previously hybridised overlap regions do not dissociate in further hybridisation steps performed at other overlap regions.

If the hybridisations shown in FIGS. 13A to 13F form part of a larger tree of hybridisations, subsequent hybridisation steps can then be performed using the result of hybridisation step $H_7$, by repeating the steps shown in FIGS. 13B/13C as often as necessary. Note that the errors in A1 and B1 which remain in one of the fragments shown in FIG. 13F would be detected in such further hybridisation steps (even though the error within A1 would become attached to the bound fragment at the next hybridisation step due to the orientation flipping from hybridisation step to hybridisation step, the error in A1 would cause a mismatch in the overlap region between A1 and the next fragment whose overlap matches A1, and so an error detection performed after the next hybridisation step would cause the other fragment to be washed away leaving the fragment containing the erroneous version of A1 orphaned so that it would not take part in subsequent hybridisations after the next hybridisation step).

On the other hand, if hybridisation step $H_7$ was actually the final hybridisation step of the tree, the fragments resulting from that hybridisation step $H_7$ would not have sticky ends (instead fragments B4, A4 would be longer to extend to the end of fragments A1, B1 respectively), and so in this case the errors in the sticky ends of the fragments shown at site 7 in FIG. 13F would in fact have been detected in the earlier error detection operations performed during hybridisation steps $H_1$ and $H_4$ as the overlap region tested in these steps would extend to the end of the fragment.

In the example of FIG. 13B, all four hybridisation steps $H_1$-$H_4$ are performed in parallel, but it would also be possible to perform them sequentially. Also, it would be possible to perform hybridisation step $H_5$ before $H_3$ or $H_4$, for example. Hence, the relative timings of the steps are not important. Nevertheless, the process can be faster by performing each level of the hybridisation tree in parallel.

While in the example of FIG. 13A to 13F, only one fragment of the assembled sequence remains error-free at site 7 following hybridisation step $H_7$, in practice a larger population of initial fragments is present at each site, so there is a larger population of fragments from which "good" fragments can be selected for pairing with other "good" fragments, so that the chances of a higher yield are improved with a larger population size. The error detection steps reduce the chance that an erroneous fragment is paired with a "good" fragment, to improve yield.

FIGS. 14A and 14B illustrate why the alternating arrangement ABBABAAB shown in FIG. 13A enables the error detection operation to exclude erroneous fragments from a subsequent hybridisation. Both diagrams show a series of hybridisations of four fragments A1, B1, A2, B2, where a further hybridisation step $H_F$ at site S2 acts on the products of two earlier hybridisation steps $H_{E1}$, $H_{E2}$ at sites S1, S2 respectively. In the comparative example of FIG. 14A, each of the hybridisation steps $H_{E1}$, $H_{E2}$, $H_F$ performs the hybridisation with the resulting hybridised fragment bound by the same strand (strand A) of the target DNA molecule. This means that even if an error is detected in hybridisation step $H_{E1}$ in fragment A1, releasing B1 in the error detection operation does not eliminate the error, and as the overlap region exposed at site S2 in hybridisation step $H_F$ is B2, this can still hybridise to the erroneous fragment A1 in the further hybridisation step $H_F$, so as to pollute the population of "good" A2-B2 fragments remaining following hybridisation step $H_{E2}$. This is because with the arrangement shown in FIG. 14A, the overlap region at which hybridisation takes place at the subsequent hybridisation step $H_F$ corresponds to the bound end of the A1-B1 fragment hybridised at step $H_{E1}$, and the sticky end of A1 at that bound end will remain intact regardless of whether an error is detected in the A1-B1 overlap region.

In contrast, as shown in FIG. 14B, by alternating the initial arrangement of fragments so that the fragments are bound to the reaction surface at opposite strands between successive sites, the further hybridisation step $H_F$ bonds one fragment which was previously error tested when bound to the reaction site via strand A with another fragment which was error tested when bound to the reaction site via strand B. Because of the sense/antisense flip, nucleotides that were previously nearest the surface and unhybridised are now present at the top of the fragment, ready for the next hybridisation step. This means that even if the error in hybridisation steps $H_{E1}$ is in the bound strand A not the loose strand B, as the remaining fragment A1 does not match the overlap region (A2-B1) exposed at the next hybridisation step $H_F$ and the fragment which would bond to that overlap region (B1) is missing as it was discarded, hybridisation of the orphaned A1 strand with the A2-B2 fragments at site S2 is prevented. Similarly, if an error was detected in the overlap region of B2 at hybridisation steps $H_{E2}$, it would have been prevented from bonding with "good" A1-B1 fragments resulting from hybridisation steps $H_{E1}$ because the A2 fragment needed to bond with the overlap region of B1 would be missing. Hence, the alternating of the pattern of arrangement of initial fragments in the ABBABAAB etc. pattern described above enables the error detection to suppress hybridisation of previously detected erroneous fragments with "good" fragments at the next site.

Prediction of the impact of the binary assembly sequence discussed above on yield is difficult to model analytically, but straightforward to simulate numerically. In each 'binary' hybridisation (i.e. the steps shown in FIGS. 13B and 13C shown above) the yield is reduced by the removed erroneous fragments, but the error rate of the remaining fragments is reduced. To account for the finite probability of detecting and rejecting errors, a Monte-Carlo simulation can be used. The results are shown in FIG. 15 for the case of assembling DNA from oligonucleotides (single-stranded nucleic acid fragments) of length 100 with a 1 in 200 error rate, assuming that each hybridisation step is of the error-detecting type. As can be seen from FIG. 15, if a high proportion of errors are detected then the yield hardly drops after the first binary step. If no errors are detected, then the yield is identical to that obtained by existing pooling or sub-pooling assembly methods. Even if the error detection accuracy is moderate (e.g. as low as 35%), this still gives rise to a significant yield improvement that increases in proportion to the DNA length, as can be seen in FIG. 16 which plots the same data relative to the yield obtained by pooling (i.e. the pooled example is a flat line equal to 1, and the other lines show the ratio between the yield obtained through binary assembly with the given error rate and the yield obtained through pooling). Hence, even though the error detection operation may miss some erroneous fragments, or may reject some "good" fragments, the overall effect of even relatively low error detection accuracies is to greatly improve the yield that can be achieved by several orders of magnitude, and this improvement becomes more significant as the length of the target DNA molecule increases. While the simulation used to generate FIGS. 15 and 16 neglects yield loss through transport, the fact that error detection will also reject some oligonucleotides without errors, and other practical issues that will reduce yield, the gains in yield available become so great as the length of DNA increases that the binary approach can tolerate significant loss due to these practicalities without losing its dramatic benefit.

As discussed above, the binary assembly sequence can be implemented using thermally addressable arrays that operate within a continuous flow. The oligonucleotides can be synthesised in place on the reaction sites, or pre-synthesised and then attached to the individual reaction sites. Release from the substrate can be achieved by either chemical or enzymatic reactions that have a reaction rate that is highly sensitive to temperature. Flow, and optionally electric or magnetic fields, or electric or magnetic traps, are then used as the driving mechanism to implement transport between reaction sites, resulting in many parallel lanes of assembly. The lack of permanent physical boundaries between reaction sites in each lane enables the pair-wise transport and hybridisation of binary assembly to proceed entirely within the flow cell in a streamlined and integrated process.

However, it is not essential to use fluid flow as the transport mechanism, and FIG. 17 shows an alternative where each reaction site may correspond to a well or container with physical barriers between adjacent containers, and manual or automatic-controlled pipetting may be used to transfer fragments from one container to the next when required. Fragments may be grown in the wells (e.g. by the oligonucleotide preparation techniques discussed above), or grown separately and then anchored to each well afterwards. The fragments may be bound to the surface of the container by a cleavable link mechanism which can be detached when required (by applying chemical reagents or enzymes, for example). Error detection can be performed using the same mechanism described above, by heating to just below the expected melt temperature of the relevant overlap region. Erroneous fragments whose bonds have been weakened can be washed away by washing the container through with fluid before detaching the remaining fragments and transferring them to the next reaction container. Another approach for transporting fragments between reaction sites could be to provide magnetic beads for each reaction site and use magnetic fields to physically move the reaction sites to bring different combinations of fragments together.

The error detection method discussed above tests the strength of bonds between partially hybridised oligonucleotides and double-stranded DNA. This is possible because the temperature at which the bonds melt, or separate, is predictable and sequence dependent. For example, the top part of FIG. 18 shows an example of a desired DNA sequence (only the sense strand is shown for conciseness). As shown in the middle part of FIG. 18, this DNA sequence can be broken at the 34$^{th}$ and 67$^{th}$ positions to form oligonucleotides s1, a1, s2, a2 (s refers to sense and a to antisense). The desired sequence can then be assembled in 3 hybridisations as shown at the bottom of FIG. 18, where the unique overlap sequence at each hybridisation results in a different melting temperature. Note that the 3 overlap regions could be hybridised in a different order to the one shown in the example of FIG. 18.

The melt temperature is the temperature at which 50% of the bonds have been broken, and there is an increasing reduction in the percentage of remaining bonds (% helicity) with temperature. FIG. 19 shows how the helicity of the three overlapping regions varies with temperature, a graph commonly referred to as a melt curve.

There are multiple error mechanisms that need to be detected:

```
1.  Mis-incorporation of nucleotides (e.g.
    ACGGTGA . . . instead of ATGGTGA . . . for s1)

2.  Truncations (e.g. ATGGTGAGCAAGG (SEQ ID NO: 7)
    for s1, truncated after the 13th base)

3.  Deletions (e.g. ATGGGA . . . instead of
    ATGGTGA . . . for s1)

4.  Insertions (e.g. ATGGATGA . . . instead of
    ATGGTGA . . . for s1)
```

Of these, mis-incorporations are the most challenging to detect as they result in a single mismatched nucleotide; the other error types usually result in more than one mismatched nucleotide and so are easier to detect. Considering just the effect of a single mismatch in a hybridised region, there are three possible erroneous nucleotides at each position, resulting in a distribution of melt temperatures for all possible incorrect overlap sequences. If the temperature of the reaction site is raised to just below the melt temperature of the correct overlap, say 0.5° C. below, then any incorrect overlaps that have a melt temperature that has been reduced by 0.5° C. or more should separate and be removed by the flow. The cumulative distribution of reduction in melt temperature of the incorrect overlaps relative to that of the correct sequence is shown in FIG. 20, and can be used to estimate the fraction of possible errors that would be detected by a 0.5° C. temperature drop (or any other desired temperature margin) relative to the expected melt temperature of an error-free fragment, and therefore the percentage of errors that would be detected if the error positions are randomly distributed.

From FIG. 20, we can make three observations:
1) For these 3 overlaps, most of the possible errors give melt temperature differences greater than 0.5° C., and so the probability of detecting a random error is high.
2) That probability is dependent on the sequence of the overlap, e.g. see the legend in FIG. 20 which shows the probability of detecting erroneous fragments with a melt temperature difference of 0.5° C.
3) A small fraction of possible errors increases the melt temperature (see the region 40 indicated in FIG. 20), and is therefore not detectable by this technique. This is because of the relatively higher bond strength of the GC bonds than the AT bonds.

Of course, detection and rejection does not simply occur in an absolute sense for any bond that has a reduced melt temperature, because of the gradual reduction in bond strength with temperature shown in the melt curves in FIG. 19. Instead, the "test" temperature of the reaction site can be chosen to maximise the ratio of helicity reduction when the melt temperature is reduced by a margin (by 0.5° C. in this example) to the unwanted helicity reduction in "good" fragments with no errors in the overlap region. This is essentially the ratio of the average fraction of "bad" (erroneous overlaps) to "good" (correct overlaps) detections, or the concentration ratio of correct overlaps. Choosing different optimal temperatures for each overlap, the cumulative distribution of resulting concentrations over all possible errors is shown in FIG. 21, with average ratios around 1.3 times (i.e. 1.3 times as many erroneous fragments as "good" fragments can be rejected by the error detection test). The ability to detect errors improves as the precision of temperature control increases; FIG. 22 shows how the average concentration ratios increase as the proceeding analysis is repeated with smaller temperature differences (i.e. the 0.5° C. assumption is varied). The analysis shown in FIGS. 20-22 shows the most difficult error type to detect (mis-incorporations). For other types of error the average "bad"-to-"good" rejection ratio will be higher as these cause more than one mismatching base in the overlap region so that the bonds in erroneous fragments are weaker than erroneous fragments with a single mis-incorporation, and can more easily be detected and rejected by the error detection operation.

The overall concentration ratio of error-free overlaps depends on the relative probabilities of the different error mechanisms, and how many base-pair mismatches they produce. Provided that the concentration ratio is greater than unity for the most difficult mis-incorporation case analysed here, there will always be some concentration of error-free overlaps or rejection of erroneous overlaps. Whilst it is therefore not practical to quantify the complete error detection efficacy from this analysis, it is possible to use the single-base mismatch concentration ratio as a relative measure between different overlap sequences, and therefore different partitions of the target DNA sequence (i.e. the nucleotide positions that the sequence is broken into oligonucleotides).

To compare the effect of sequence partitioning on error detection efficacy, FIG. 23 shows the cumulative distribution of averaged single-base mismatch concentration ratio across the three overlaps over all possible partitions of the previous DNA sequence, given constraints of oligonucleotide length 20 to 80 and overlap region length 20 to 40. As can be seen from FIG. 23, there is significant benefit in error detection ability to be obtained by selecting the partitioning of the sequence appropriately—by using partitions in region 50 instead of those in region 60, the error detection ability can be improved (and false positive detection rate reduced). A small number of optimal partitions will give a concentration ratio that is higher than would be obtained by traditional partitioning methods that did not take this into account. This example is for a short DNA sequence; as the sequence length increases the importance of optimising the partitioning in this way increases. Of course, DNA partitioning may also account for other restrictions, such as minimisation of secondary structure and avoidance of local concentration of GC content. Maximising error detection ability in this way may therefore be just one parameter in a multi-variable optimisation. But in general, selecting the partition points for dividing the target DNA sequence into initial fragments so that (a) the average melt temperature difference between "good" and "bad" fragments is at least a predetermined threshold, and (b) the partitions are the ones that achieve as high as possible "bad"-to-"good" rejection ratio (when taking into account other restrictions as discussed above), can enable better error detection performance.

Also, the simulation of "bad"-to-"good" rejection ratios can also enable bespoke temperature margins for each reaction site, depending on the average melt temperature difference between erroneous fragments and "good" fragments for a given overlap region—for overlap regions with a larger melt temperature difference, the temperature margin (difference between the expected melt temperature and the temperature to which the reaction site is heated and the expected melt temperature) can be larger than for overlap regions with a smaller melt temperature difference, in order to improve the "bad"-to-"good" rejection ratio by rejecting fewer "good" fragments.

Some examples may provide a method for forming multiple instances of a target double-stranded nucleic acid molecule from a plurality of sets of single-stranded nucleic acid fragments, each set comprising multiple instances of a respective portion of the target double-stranded nucleic acid molecule, the method comprising:

providing each set of single-stranded nucleic acid fragments at respective reaction sites of an apparatus comprising a lane of reaction sites; and performing a plurality of hybridisation steps, in which each hybridisation step is performed at a given reaction site of the lane and comprises:

selectively detaching the single-stranded nucleic acid fragments provided at a previous reaction site, or double-stranded nucleic acid fragments hybridised in a previous hybridisation step performed at a previous reaction site, from the surface of the previous reaction site;

transporting the detached single-stranded or double-stranded nucleic acid fragments from said previous reaction site to said given reaction site; and hybridising the transported fragments with further single-stranded fragments provided at the given reaction site or with double-stranded fragments hybridised in a previous hybridisation step performed at the given reaction site, to form double-stranded fragments.

In such examples, the apparatus may also comprise a fluid flow element configured to direct flowing fluid over the lane of reaction sites, and the transport of the detached single-stranded or double-stranded nucleic acid fragments from the previous reaction site to the given reaction site may be performed by transport in the flowing fluid provided by the fluid flow element. Each set of single-stranded nucleic acid fragments (corresponding to a different portion of the target double-stranded nucleic acid molecule) may be grown at the corresponding one of the reaction sites before performing the hybridisation steps.

Further example arrangements are set out in the following clauses:

(1) A method of providing multiple instances of a target double-stranded nucleic acid from a plurality of nucleic acid fragments, comprising:

a plurality of initial hybridisation steps, each initial hybridisation step comprising hybridising respective pairs of partially overlapping nucleic acid fragments to form a plurality of hybridised fragments; and one or more further hybridisation steps, each further hybridisation step corresponding to a pair of earlier hybridisation steps and comprising hybridising respective pairs of partially overlapping hybridised fragments which are the direct product of the pair of earlier hybridisation steps to form longer hybridised fragments, where each of the pair of earlier hybridisation steps comprises one of the initial hybridisation steps or one of the further hybridisation steps;

wherein said one or more further hybridisation steps comprise at least one further hybridisation step for which both of the corresponding pair of earlier hybridisation steps comprise an error-detecting type of hybridisation step;

the error-detecting type of hybridisation step comprising:

performing an error detecting operation to detect whether the hybridised fragments formed in the error-detecting type of hybridisation step comprise at least one erroneous hybridised fragment comprising at least one mismatching base pair in an overlap region hybridised in the error-detecting type of hybridisation step; and discarding at least part of said at least one erroneous fragment to exclude the at least one erroneous fragment from a subsequent further hybridisation step.

(2) The method of clause (1), wherein the method is performed using an apparatus comprising at least one lane of reaction sites aligned in a predetermined direction and a fluid control element to direct a flowing fluid over each reaction site in the predetermined direction.

(3) The method of clause (2), the apparatus further comprising temperature control circuitry to independently control a temperature at each reaction site.

(4) The method of any of clauses (2) and (3), wherein the reaction sites comprise one of:

portions of a surface without a physical barrier between adjacent reaction sites, and portions of a surface with a selectively removable physical barrier between adjacent reaction sites.

(5) The method of any preceding clause, wherein at least one of the plurality of initial hybridisation steps is said error-detecting type of hybridisation step.

(6) The method of any preceding clause, wherein each initial hybridisation step is said error-detecting type of hybridisation step.

(7) The method of any preceding clause, wherein at least one of said further hybridisation steps is said error-detecting type of hybridisation step.

(8) The method of any preceding clause, wherein each further hybridisation step is said error-detecting type of hybridisation step.

(9) The method of any preceding clause, wherein said error detecting operation comprises weakening a bond between the partially overlapping fragments forming each detected erroneous hybridised fragment, and providing fluid to wash away said at least part of said at least one erroneous hybridised fragment.

(10) The method of any preceding clause, wherein said error detecting operation comprises adjusting a temperature of a reaction site on which the hybridised fragments are formed to a target temperature corresponding to a margin below an expected melting temperature of the overlap region formed in that hybridisation step for an error-free hybridised fragment.

(11) The method of clause (10), wherein partitioning of the target double-stranded nucleic acid into the nucleic acid fragments is selected such that, at each overlap region, a difference between the expected melting temperature of the overlap region in an error-free hybridised fragment and an expected melting temperature of the overlap region in an erroneous hybridised fragment with at least one base error within that overlap region is greater than a predetermined threshold.

(12) The method of clause (11), wherein said predetermined threshold is at least 0.1° C.

(13) The method of any of clauses (1) to (9), wherein said error detecting operation comprises exposing said hybridised fragments to a mismatching base pair detecting enzyme.

(14) The method of any preceding clause, wherein hybridised fragments are transported in a flowing fluid between reaction sites on which respective hybridisation steps are performed.

(15) The method of any preceding clause, wherein the target double-stranded nucleic acid comprises a first strand of single-stranded nucleic acid hybridised to a second strand of single-stranded nucleic acid; and
in each hybridisation step, the hybridised fragment of nucleic acid formed in that hybridisation step is bound to a surface of a reaction site via the first strand or the second strand.

(16) The method of clause (15), wherein one of said at least one further hybridisation step performed at a given reaction site comprises hybridising:
first hybridised fragments bound to the surface of the given reaction site via one of the first strand and the second strand; and
second double-stranded fragments formed at an earlier reaction site in an earlier hybridisation step, when bound to a surface of the earlier reaction site via the other of the first strand and the second strand.

(17) The method of any of clauses (15) and (16), wherein the initial hybridisation steps and the at least one further hybridisation step form a sequence of hybridisation steps in which for any pair of hybridisation steps in which the second hybridisation step of the pair hybridises a hybridised fragment formed in the first hybridisation step of the pair with a further fragment, the hybridised fragments formed in the pair of hybridisation steps are bound to a surface of a corresponding reaction site via opposite ones of the first strand and the second strand respectively.

(18) The method of any preceding clause, wherein in at least one of said error-detecting type of hybridisation step, remaining hybridised fragments following the error detection operation are selectively detached from a surface of a reaction site.

(19) The method of clause (18), wherein the selective detaching of the remaining hybridised fragments is temperature-controlled.

(20) The method of any of clauses (18) and (19), wherein the selective detaching of the remaining hybridised fragments comprises heating the reaction site to a predetermined detaching temperature of a linker substance binding the remaining hybridised fragments to the reaction site, where the linker substance is arranged to detach from the surface when at the predetermined detaching temperature.

(21) The method of any of clauses (18) and (19), wherein the selective detaching of the remaining hybridised fragments comprises exposing the remaining hybridised fragments to a temperature-activated detaching enzyme and adjusting a temperature of the reaction site to an activation temperature of the detaching enzyme.

(22) The method of any preceding clause, wherein each hybridisation step, other than any hybridisation step performed on a pair of single-stranded fragments, comprises a ligation operation performed on the hybridised fragments;
wherein for an error-detecting type of hybridisation step, the ligation operation is performed on the remaining double-stranded fragments excluding the at least one erroneous hybridised fragment detected in the error detection operation.

(23) The method of any preceding clause, wherein each of the plurality of nucleic acid fragments comprises at least one overlap region for overlapping with a corresponding overlap region of another of the nucleic acid fragments; and
each base of the target double-stranded nucleic acid is within one of the overlap regions of one of the plurality of nucleic acid fragments.

(24) The method of any preceding clause, comprising a step of forming the plurality of nucleic acid fragments prior to performing said plurality of initial hybridisation steps.

(25) A computer-readable program or data structure comprising instructions or control data for controlling an apparatus to perform the method of any preceding claim.

(26) A storage medium storing the program or data structure of clause (25).

Although illustrative embodiments of the invention have been described in detail herein with reference to the accompanying drawings, it is to be understood that the invention is not limited to those precise embodiments, and that various changes and modifications can be effected therein by one skilled in the art without departing from the scope and spirit of the invention as defined by the appended claims.

The invention claimed is:

1. A method of hybridising a plurality of nucleic acid fragments, comprising:
   a plurality of initial hybridisation steps, each initial hybridisation step comprising hybridising respective pairs of partially overlapping nucleic acid fragments to form a plurality of hybridised fragments; and
   one or more further hybridisation steps, each further hybridisation step comprising hybridising respective pairs of partially overlapping hybridised fragments which are the direct products of a corresponding pair of earlier hybridisation steps to form longer hybridised fragments, where each of the pair of earlier hybridisation steps comprises one of the initial hybridisation steps or one of the further hybridisation steps;
   wherein said one or more further hybridisation steps comprise at least one further hybridisation step for which both of the corresponding pair of earlier hybridisation steps comprise an error-detecting type of hybridisation step;
   the error-detecting type of hybridisation step comprising:
      performing an error detecting operation to detect whether the hybridised fragments formed in the error-detecting type of hybridisation step comprise at least one erroneous hybridised fragment comprising at least one mismatching base pair in an overlap region hybridised in the error-detecting type of hybridisation step; and
      discarding at least part of said at least one erroneous fragment to exclude the at least one erroneous fragment from a subsequent further hybridisation step;
   wherein
      in each hybridisation step, the hybridised fragment of nucleic acid formed in that hybridisation step comprises a first strand of single-stranded nucleic acid hybridized to a second strand of single-stranded nucleic acid and is bound to a surface of a reaction site via the first strand or the second strand.

2. The method of claim 1, wherein one of said at least one further hybridisation step performed at a given reaction site comprises hybridising:
   first hybridised fragments bound to the surface of the given reaction site via one of the first strand and the second strand; and
   second double-stranded fragments formed at an earlier reaction site in an earlier hybridisation step, when bound to a surface of the earlier reaction site via the other of the first strand and the second strand.

3. The method of claim 1, wherein the initial hybridisation steps and the at least one further hybridisation step form a sequence of hybridisation steps in which for any pair of hybridisation steps in which the second hybridisation step of the pair hybridises a hybridised fragment formed in the first hybridisation step of the pair with a further fragment, the hybridised fragments formed in the pair of hybridisation steps are bound to a surface of a corresponding reaction site via opposite ones of the first strand and the second strand respectively.

4. The method of claim 1, wherein the method is performed using an apparatus comprising at least one lane of reaction sites aligned in a predetermined direction and a fluid control element to direct a flowing fluid over each reaction site in the predetermined direction.

5. The method of claim 4, the apparatus further comprising temperature control circuitry to independently control a temperature at each reaction site.

6. The method of claim 4, wherein the reaction sites comprise one of:
   portions of a surface without a physical barrier between adjacent reaction sites, and
   portions of a surface with a selectively removable physical barrier between adjacent reaction sites.

7. The method of claim 1, wherein at least one of the plurality of initial hybridisation steps is said error-detecting type of hybridisation step.

8. The method of claim 1, wherein each initial hybridisation step is said error-detecting type of hybridisation step.

9. The method of claim 1, wherein at least one of said further hybridisation steps is said error-detecting type of hybridisation step.

10. The method of claim 1, wherein each further hybridisation step is said error-detecting type of hybridisation step.

11. The method of claim 1, wherein said error detecting operation comprises weakening a bond between the partially overlapping fragments forming each detected erroneous hybridised fragment, and providing fluid to wash away said at least part of said at least one erroneous hybridised fragment.

12. The method of claim 1, wherein said error detecting operation comprises adjusting a temperature of a reaction site on which the hybridised fragments are formed to a target temperature corresponding to a margin below an expected melting temperature of the overlap region formed in that hybridisation step for an error-free hybridised fragment.

13. The method of claim 12, wherein partitioning of a target double-stranded nucleic acid, which is produced by a final hybridisation step, into the nucleic acid fragments is selected such that, at each overlap region, a difference between the expected melting temperature of the overlap region in an error-free hybridised fragment and an expected melting temperature of the overlap region in an erroneous hybridised fragment with at least one base error within that overlap region is greater than a predetermined threshold.

14. The method of claim 13, wherein said predetermined threshold is at least 0.1° C.

15. The method of claim 1, wherein said error detecting operation comprises exposing said hybridised fragments to a mismatching base pair detecting enzyme.

16. The method of claim 1, wherein hybridised fragments are transported in a flowing fluid between reaction sites on which respective hybridisation steps are performed.

17. The method of claim 1, wherein in at least one of said error-detecting type of hybridisation step, remaining hybridised fragments following the error detection operation are selectively detached from a surface of a reaction site.

18. The method of claim 17, wherein the selective detaching of the remaining hybridised fragments is temperature-controlled.

19. The method of claim 17, wherein the selective detaching of the remaining hybridised fragments comprises heating the reaction site to a predetermined detaching temperature of a linker substance binding the remaining hybridised fragments to the reaction site, where the linker substance is arranged to detach from the surface when at the predetermined detaching temperature.

20. The method of claim 17, wherein the selective detaching of the remaining hybridised fragments comprises exposing the remaining hybridised fragments to a temperature-activated detaching enzyme and adjusting a temperature of the reaction site to an activation temperature of the detaching enzyme.

21. The method of claim 1, wherein each hybridisation step, other than any hybridisation step performed on a pair of single-stranded fragments, comprises a ligation operation performed on the hybridised fragments;

wherein for an error-detecting type of hybridisation step, the ligation operation is performed on the remaining double-stranded fragments excluding the at least one erroneous hybridised fragment detected in the error detection operation.

22. The method of claim 1, wherein each of the plurality of nucleic acid fragments comprises at least one overlap region for overlapping with a corresponding overlap region of another of the nucleic acid fragments; and each base of a target double-stranded nucleic acid produced by a final hybridisation step is within one of the overlap regions of one of the plurality of nucleic acid fragments.

23. The method of claim 1, comprising a step of forming the plurality of nucleic acid fragments prior to performing said plurality of initial hybridisation steps.

* * * * *

SEQUENCE LISTING

```
<160> NUMBER OF SEQ ID NOS: 7

<210> SEQ ID NO 1
<211> LENGTH: 40
<212> TYPE: DNA
<213> ORGANISM: Artificial Sequence
<220> FEATURE:
<223> OTHER INFORMATION: example target DNA sequence

<400> SEQUENCE: 1
gaacatgtcg agcaggtacg gctctcacta gggccgccgc                                40
```

```
<210> SEQ ID NO 2
<211> LENGTH: 100
<212> TYPE: DNA
<213> ORGANISM: Artificial Sequence
<220> FEATURE:
<223> OTHER INFORMATION: desired DNA sequence

<400> SEQUENCE: 2
atggtgagca agggcgagga gctgttcacc ggggtggtgc ccatcctggt cgagctggac      60
ggcgacgtaa ggagctgttc accggggtgg tgaggagctg                          100

<210> SEQ ID NO 3
<211> LENGTH: 34
<212> TYPE: DNA
<213> ORGANISM: Artificial Sequence
<220> FEATURE:
<223> OTHER INFORMATION: oligonucleotide s1

<400> SEQUENCE: 3
atggtgagca agggcgagga gctgttcacc gggg                                 34

<210> SEQ ID NO 4
<211> LENGTH: 67
<212> TYPE: DNA
<213> ORGANISM: Artificial Sequence
<220> FEATURE:
<223> OTHER INFORMATION: oligonucleotide a1

<400> SEQUENCE: 4
cgtcgccgtc cagctcgacc aggatgggca ccaccccggt gaacagctcc tcgcccttgc      60
tcaccat                                                               67

<210> SEQ ID NO 5
<211> LENGTH: 66
<212> TYPE: DNA
<213> ORGANISM: Artificial Sequence
<220> FEATURE:
<223> OTHER INFORMATION: oligonucleotide s2

<400> SEQUENCE: 5
tggtgcccat cctggtcgag ctggacggcg acgtaaggag ctgttcaccg ggtggtgag      60 gagctg                                                                66

<210> SEQ ID NO 6
<211> LENGTH: 33
<212> TYPE: DNA
<213> ORGANISM: Artificial Sequence
<220> FEATURE:
<223> OTHER INFORMATION: oligonucleotide a2

<400> SEQUENCE: 6
cagctcctca ccaccccggt gaacagctcc tta                                  33

<210> SEQ ID NO 7
<211> LENGTH: 13
<212> TYPE: DNA
<213> ORGANISM: Artificial Sequence
<220> FEATURE:
<223> OTHER INFORMATION: example error mechanism (truncation)

<400> SEQUENCE: 7
atggtgagca agg                                                        13
```